(12) United States Patent
Johnson et al.

(10) Patent No.: US 8,128,631 B2
(45) Date of Patent: Mar. 6, 2012

(54) APPARATUS AND METHOD FOR PLACING AN IMPLANT IN VIVO

(75) Inventors: Wesley D. Johnson, Eden Prairie, MN (US); Daryl R. Pilarski, East Bethel, MN (US)

(73) Assignee: Alexandria Research Technologies, Inc., Plymouth, MN (US)

( * ) Notice: Subject to any disclaimer, the term of this patent is extended or adjusted under 35 U.S.C. 154(b) by 925 days.

(21) Appl. No.: 11/460,549

(22) Filed: Jul. 27, 2006

(65) Prior Publication Data

US 2008/0234688 A1 Sep. 25, 2008

Related U.S. Application Data

(60) Provisional application No. 60/703,120, filed on Jul. 28, 2005.

(51) Int. Cl.
*A61B 17/58* (2006.01)
(52) U.S. Cl. .................................. 606/90; 606/91
(58) Field of Classification Search .......... 606/81, 606/90, 91; 600/587, 594, 595
See application file for complete search history.

(56) References Cited

U.S. PATENT DOCUMENTS

| | | | |
|---|---|---|---|
| 4,961,748 A | 10/1990 | Frey et al. | |
| 6,475,243 B1 * | 11/2002 | Sheldon et al. | 623/22.28 |
| 7,553,332 B2 | 6/2009 | Bacon | |
| 2003/0050645 A1 | 3/2003 | Parker et al. | |
| 2003/0236523 A1 | 12/2003 | Johnson et al. | |
| 2004/0015174 A1 | 1/2004 | Null et al. | |
| 2004/0097952 A1 | 5/2004 | Sarin et al. | |
| 2004/0102852 A1 | 5/2004 | Johnson et al. | |

FOREIGN PATENT DOCUMENTS

| | | |
|---|---|---|
| DE | 36 30 276 A1 | 3/1988 |
| EP | 0687452 A1 | 12/1995 |
| FR | 2686791 A1 | 8/1993 |
| FR | 2834630 A1 | 7/2003 |
| JP | 8-510945 | 11/1996 |
| JP | 2003-534096 | 11/2003 |
| JP | 2005-518831 | 6/2005 |
| WO | WO 2004/017870 A1 | 3/2004 |
| WO | WO 2004-069107 | 8/2004 |

OTHER PUBLICATIONS

Extended European Search Report, issued Jun. 1, 2011, regarding related European Patent Application Serial No. 06788766.1; European Patent Office.

* cited by examiner

*Primary Examiner* — Thomas C. Barrett
*Assistant Examiner* — Nicholas Woodall
(74) *Attorney, Agent, or Firm* — Barbara A. Wrigley; Oppenheimer Wolff & Donnelly, LLP

(57) ABSTRACT

A system and method for placing an implant into or onto supporting bone, or between adjacent bones, without impaction is disclosed. The system includes an implant, a distracter, and a sleeve. Optionally, the invention includes an alignment guide, a surgical navigational tracker, and a bone displacer. The sleeve is structured to interpose the implant and supporting bone and provide a differential engagement force between the sleeve-implant interface and the sleeve-bone interface to preferentially move the implant into, onto or between supporting bone structures.

58 Claims, 17 Drawing Sheets

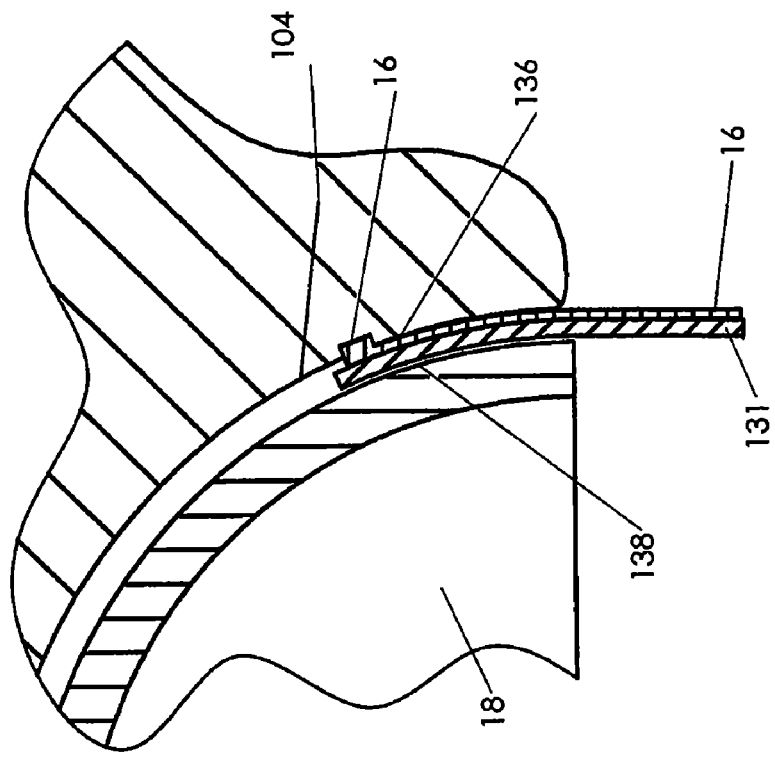
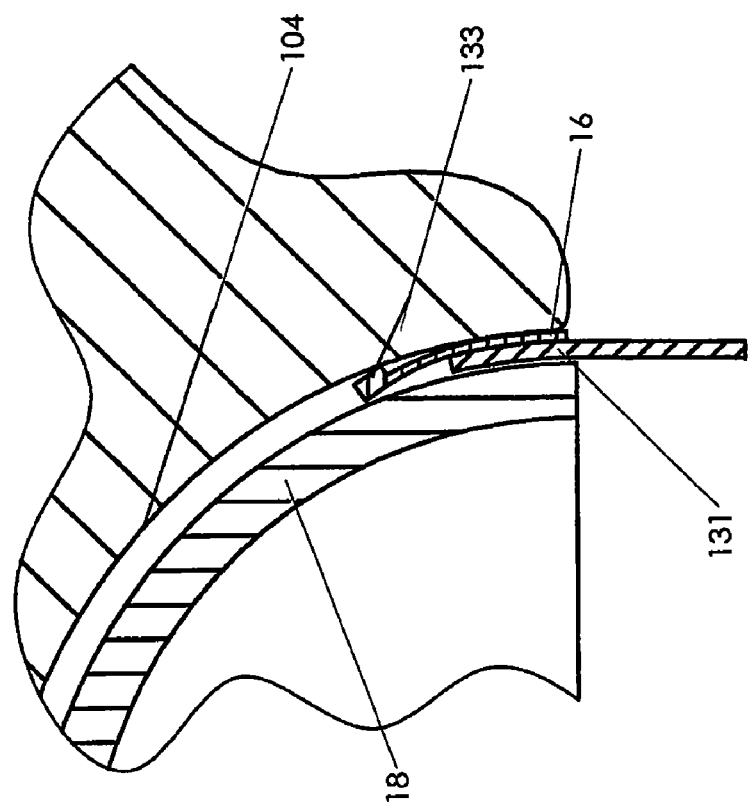

APPARATUS AND METHOD FOR PLACING AN IMPLANT IN VIVO

CROSS REFERENCE TO RELATED APPLICATIONS

This application is based on and claims the benefit of U.S. Provisional Application No. 60/703,120, filed Jul. 28, 2005, the entirety of which is hereby incorporated by reference.

BACKGROUND OF THE INVENTION

1. Field of the Invention

This invention relates to implants and instruments for use in orthopaedic surgery. More particularly, this invention relates to a device and method for aligning, orienting and placing an implant into or onto supporting bone, or between adjacent bones without impaction.

2. Description of the Related Art

The field of orthopaedic surgery includes joint arthroplasty, spinal disc replacement, spinal interbody fusion, vertebral compression fracture reduction and realignment osteotomies. Joint arthroplasty includes partial and total replacement of the bony support surfaces of articulating joints, to include knee, hip, shoulder, spinal facet, ankle, toe, finger, wrist and elbow. Spinal disc replacement includes partial and total replacement of the bony support surfaces of vertebral bodies, which are the endplates, and the annulus, the nucleus and combinations thereof. Within the specification reference is made to a spinal motion segment which is the combination of structures providing motion between adjacent vertebral bodies, that is two facet joints and a spinal disc. For the purposes of this specification, the term "Kinematic Restoration" will be used to broadly refer to joint arthroplasty, as defined above, and spinal disc replacement, as defined above, in human and in veterinarian applications.

In a healthy articulating joint, a smooth and resilient surface consisting of articular cartilage covers the bony structures to provide bone support surfaces. In a healthy spinal disc, vertebral body endplates provide bone support surfaces for the interposed annulus and nucleus. The annulus is attached to adjoining vertebral body endplates. Articulating joints and spinal discs generally consist of two or more relatively rigid bone structures that maintain a kinematic and dynamic relationship one to the other. Soft tissue structures spanning or interposed between the bone structures hold the bone structures together and aid in defining the motion or kinematics of one bone structure to the other.

The bone support surfaces, as described for articulating joints and for spinal discs, work in combination with the soft tissue structures spanning or interposed between them to form a mechanism that defines the envelop of motion of adjacent bone structures one to the other. Within a typical envelop of motion, the bone structures move in a predetermined pattern with respect to one another. When articulated to the limits of soft tissue constraint, the motion defines a total envelop of motion between the bony structures. Arthritis, degeneration, trauma and other pathologies lead to pain, deformity and compromised motion in articulating joints and in spinal discs.

Orthopaedic surgery includes Kinematic Restoration procedures as described above which relieve pain, correct deformity and restore motion in pathologic articulating joints and spinal discs. It is typical in such procedures to impact one or more implants into or onto the bone support surfaces or between adjacent bone support surfaces. One or more of the related bone support surfaces are prepared to receive one or more implants, such implants being placed and forcibly impacted therein, thereon or there between such bone support surfaces.

Spinal interbody fusion involves removal of a pathological nucleus, preparing the endplates to form bone support surfaces and includes placement of one or more implants, either of synthetic material, allograft bone, autograft bone or a combination thereof, between adjacent vertebral bodies to facilitate fusion between the vertebral bodies. Vertebral compression fracture reduction involves creating a cavity in the vertebral body to form bone support surfaces and includes placement of one or more implants.

Suitable synthetic materials for the implants described above include cobalt chromium alloys, titanium and titanium alloys, stainless steel, zerconia, alumina and other ceramic materials, polyethylene, urethanes, PEEK, carbon fiber filled PEEK, calcium based composites, Nitinol, and polymethylmethacrylate.

Orthopaedic implants for Kinematic Restoration can be secured to bone with cement or grouting material, by bone ingrowth or ongrowth, or by biologic materials. In the case of ingrowth or ongrowth, or biologic fixation, a close and stable fit between implant and supporting bone is required to promote positive bone remodeling. Such a fit has traditionally been attained by press-fitting the implant into, onto or between supporting bone. In the case of placing an implant into supporting bone for bone ingrowth or ongrowth, for example an acetabular cup in total hip replacement, the acetabulum is prepared and a corresponding cup size is selected to provide a line to line fit or a press-fit between the cup and the prepared acetabulum. Alternatively, if an implant is to be fitted over a supporting bone for bone ingrowth or ongrowth, for example the femoral component of a total knee replacement, the distal femur is prepared and a corresponding femoral component size is selected to provide a line to line fit or a press-fit between the femoral component and the prepared femur. The implant is held in position by an impaction device and impacted into place with a mallet. Such impaction is traumatic. Alternatively, if an implant is to be fitted between adjacent bones for bone ingrowth or ongrowth, for example a spinal disc replacement, the involved endplates are prepared and a corresponding disc replacement size is selected to provide proper height and tension of the interbody space. The implant may be held in position by an impaction device and impacted into place with a mallet. Such impaction is traumatic. Alternatively, the interbody space may be overly distracted to place the implant. Such over distraction is traumatic.

In surgical procedures relying on surgical navigation to aid the surgeon in restoring alignment and in aligning and positioning implants, such impaction may loosen and move navigational trackers introducing error in the surgical navigation of the procedure. In addition, subsequent impactions may alter alignment of the implant relative to supporting bone. Implant alignment is critical for long term function and durability of the implant.

Similarly, in spinal interbody fusion, vertebral compression fracture reduction and realignment osteotomy procedures a close and stable fit between implant and supporting bone is required to promote positive bone remodeling. Such a fit has traditionally been attained by press-fitting the implant between adjacent bones or into a supporting bone. The implant is held in position by an impaction device and impacted into place with a mallet. Such impaction is traumatic. Alternatively, the receiving site, either between adjacent bones for spinal interbody fusion, or within a bone for vertebral compression fracture reduction or realignment osteotomies, requires over distraction of the receiving site to place the implant. Such over distraction is traumatic.

There exists a need for a device and method to accurately align and orient an implant with the supporting bone. There also exists a need for a device and method to place an implant into, onto or between supporting bone without impaction or over distraction.

BRIEF SUMMARY OF THE INVENTION

The present invention provides a system and method for implant placement into or onto a supporting bone, or between adjacent bones, which involves less or minimally invasive surgical procedures. The present invention further provides a system and method to accurately align and orient an implant. Optionally, the present invention further provides an apparatus and method to displace adjacent bones while placing an implant onto or into one or more of the bones, or between the bones. The present invention provides an apparatus for placing an implant within a prepared bone cavity, over a prepared bone surface, or between prepared surfaces of adjacent bones wherein the implant is structured to press-fit into, onto or between the supporting bone or bones to provide initial implant stability, anatomical alignment and appropriate relative position of the supporting bone or bones. The implant having a final seated position relative to supporting bone or bones, when in such position the implant is placed properly in supporting bone or bones and the supporting bone restricts further advancement of the implant. As used herein, the following terms have the following definitions:

Orienting—For the purposes of the present invention orientating pertains to 1) orientating sub-components of an implant to one another, and 2) orientating implant components of a Kinematic Restoration to one another. In both cases orientating means to bring the parts into working relationship to one another so that the assembly of parts functions as intended.

Aligning—For the purposes of the present invention aligning pertains to 1) alignment of sub-components of an implant to supporting bone, such supporting bone being properly aligned, and 2) alignment of implant components of a Kinematic Restoration to supporting bone. In both cases aligning means to bring the parts into correct relative position with respect to the supporting bone so that the arthroplasty functions as intended.

Implant component and sub-component—For the purposes of the present invention an implant component refers to the parts that make up the arthroplasty, for example femoral, tibial and patellar components make up a total knee arthroplasty. Sub-component refers to the parts that make up the implant component. Each component may be unitary in construction, or may include a plurality of sub-components. Reference made to an "implant" refers to one or more of the components, or one or more of the sub-components, or a combination thereof.

Engagement force—For purposes of the present invention, the term "engagement force" as it relates to the sleeve to implant interface and to the sleeve to bone interface shall be defined as the force tending to slide a surface along another at which relative motion between the surfaces starts. Such engagement force may be provided by a number of mating surface structures to include frictional interference, ridges, grit blast, chemically etched, corrugated or patterned between the surfaces wherein the magnitude of the engagement force may be established by providing an appropriate coefficient of friction between the adjacent surfaces; engagement between adjoining surfaces, such engagement being mechanical interlock, releasable mechanical interlocks, pined interface, releasable pined interface, bonding of the interface, or other suitable means to restrain relative movement between two or more parts. Wherein the restraint has a threshold that when reached the parts move relative to one another, that threshold being the engagement force. The sleeve to implant interface and the sleeve to bone interface are under compression because the sleeve in the present invention is interposed between the implant and supporting bone and the implant is structured to provide a press-fit with supporting bone.

Joint Arthroplasty—For the purposes of this specification, the term "joint arthroplasty" includes partial and total replacement of the bony support surfaces of articulating joints, to include knee, hip, shoulder, spinal facet, ankle, toe, finger, wrist and elbow.

Spinal Disc Replacement—For the purposes of this specification, the term "spinal disc replacement" includes partial and total replacement of the bony support surfaces of vertebral bodies, which are the endplates, and the annulus, the nucleus and combinations thereof.

Spinal Motion Segment—For the purposes of this specification, the term "spinal motion segment" is the combination of structures providing motion between adjacent vertebral bodies, that is two facet joints and a spinal disc.

Kinematic Restoration—For the purposes of this specification, the term "kinematic restoration" will be used to broadly refer to joint arthroplasty, as defined herein, and spinal disc replacement, as defined above, in human and in veterinarian applications.

The present invention is comprised of an implant, a distracter, and a sleeve. The distracter is structured to provide a gradual insertion force to move the implant into, onto or between supporting bone or bones with the insertion force reacted by the supporting bone or bones. The sleeve is structured to interpose the implant and supporting bone and provide a differential engagement force between the sleeve-implant interface and the sleeve-bone interface to preferentially move the implant into, onto or between supporting bone structures. Optionally, the present invention may include an alignment guide. Alternatively, the present invention may include a surgical navigational tracker. The alignment guide is structured to orient and align the implant. Alternatively, the navigational tracker is structured to orient and align the implant. Optionally, the present invention may include a bone displacer structured to distract adjacent bones or adjacent bone support surfaces to facilitate placement of an implant.

The implant structured for use in Kinematic Restoration, spinal interbody fusion, vertebral compression fracture reduction or realignment osteotomy The sleeve structured to:
interpose implant and bone or bones,
to be of unitary construction,
alternatively, to be a plurality of sleeves,
to have a first surface structured to engage an implant (i.e. implant engagement),
to have a second surface structured to engage a bone or bones (i.e. bone engagement).

The distracter structured to:
connect to an implant (i.e. implant connection),
alternatively, connect to bone or bones (i.e. bone connection),
connect to a sleeve or plurality of sleeves (i.e. sleeve connection),
displace the implant relative to the sleeve,
displace the sleeve relative to the bone or bones,
displace the implant relative to the bone or bones.

In one embodiment of the present invention the distracter and sleeve are structured to place an implant between adjacent first and second bones, wherein:
   the distracter is connected to the implant and to the sleeve,
   the sleeve has a first surface structured to engage the implant and a second surface structured to engage the first and second bones,
   the sleeve to bone engagement force being greater than the sleeve to implant engagement force,
   the distracter structured to displace the implant towards the implant's final seated position during which the sleeve to bone engagement force has not been exceeded and the relative position of the sleeve to the first and second bone does not significantly change,
   the implant is advanced to it's final seated position at which point the first and second bone restrict further advancement of the implant,
   continued displacement of the distracter then overcomes the sleeve to bone engagement force and the sleeve is moved away from the implant's final seated position and out of the implant to bone interface,
   the sleeve and distracter are then removed and the implant is in proper position.

In an alternative embodiment of the present invention the distracter and sleeve are structured to place an implant into a bone cavity, wherein:
   the distracter is connected to the implant and to the sleeve,
   the sleeve has a first surface structured to engage the implant and a second surface structured to engage the bone cavity,
   the sleeve to bone engagement force being greater than the sleeve to implant engagement force,
   the distracter structured to displace the implant towards the implant's final seated position during which the sleeve to bone engagement force has not been exceeded and the relative position of the sleeve to bone cavity does not significantly change,
   the implant is advanced to it's final seated position at which point the bone restricts further advancement of the implant,
   continued displacement of the distracter then overcomes the sleeve to bone engagement force and the sleeve is moved away from the implant's final seated position and out of the implant to bone interface,
   the sleeve and distracter are then removed and the implant is in proper position.

In yet another embodiment of the present invention the distracter and sleeve are structured to place an implant onto a bone, wherein:
   the distracter is connected to the bone and to the sleeve,
   the sleeve has a first surface structured to engage the implant and a second surface structured to engage the bone,
   the sleeve to bone engagement force being lower than the sleeve to implant engagement force,
   the distracter structured to displace the sleeve towards the implant's final seated position during which the sleeve to implant engagement force has not been exceeded and the relative position of the sleeve to implant does not significantly change,
   the implant is advanced to it's final seated position at which point the bone restricts further advancement of the implant,
   continued displacement of the distracter then overcomes the sleeve to implant engagement force and the sleeve is moved away from the implant's final seated position and out of the implant to bone interface,
   the sleeve and distracter are then removed and the implant is in proper position.

Optionally, each of the embodiments described above may include an alignment guide structured to:
   attach to the inserter,
   alternatively, attach to the sleeve,
   alternatively, attach to the implant,
   alternatively, attach to one or more of the supporting bones,
   provide alignment rods aligned with anatomic features or implant features to provide a geometric reference between the implant and one or more of the supporting bones to align and orient the implant.

Optionally, each of the embodiments described above may include a surgical navigational tracker structured to:
   attach to the inserter,
   alternatively, attach to the sleeve,
   alternatively, attach to the implant,
   alternatively, attach to one or more of the supporting bones,
   support reflective spheres typically used with optical surgical navigation system. Alternatively, to support electromagnetic targets typically used with electromagnetic surgical navigation systems.
   be navigated by the surgical navigation system to aid the surgeon in orienting and aligning the implant and to provide a geometric reference between the implant and one or more of the supporting bones to align and orient the implant.

Optionally, each of the embodiments described above may include a bone displacer structured to:
   attach to the distracter,
   alternatively, be integral with the distracter,
   attach to one or more of the supporting bones,
   attach to the implant,
   distract adjacent bones away from one another,
   alternatively, distract the distracter away from one or more adjacent bones,
   alternatively, distract the implant away from one or more adjacent bones.

The distracter and the bone displacer are structured as hydraulic cylinders each having a piston and cylinder actuated by fluid or air pressure. Alternatively, the distracter or bone displacer may be mechanically actuated by screw mechanisms, scissors mechanisms, lever and fulcrum mechanisms, spring mechanisms, bladders, balloons, bellows, gear mechanisms, rack and pinion mechanisms, and other expandable devices or other elements that provide a force between two or more objects, or combinations thereof.

The structure of the connections between the distracter and sleeve, distracter and implant, and distracter and bone described above and the structure of the connections between the bone displacer and distracter, bone displacer and bone, and bone displacer and implant, include compressive contact surfaces, threaded interfaces and threaded fasteners, pinned interfaces, "T" slots; dovetail locks; cylindrical interlocks; button interlocks; spherical interlocks; trinkle locks; or a combination of these, or other connecting means used to connect two or more parts.

Suitable materials for the sleeve as described above and in the detailed description of the invention include cobalt-chromium alloy, stainless steel, titanium, titanium alloys, Nitinol, plastics, including but not limited to urethane, polyethylene and expanded polyethylene, nylon, woven fabric materials, and the like.

The invention will be further described with reference to the following detailed description taken in conjunction with the drawings.

BRIEF DESCRIPTION OF THE DRAWINGS

FIG. 3 is a cross sectional view showing a cup placed into a cup sleeve and placed into a prepared acetabulum in accordance with the present invention.

FIG. 4 is a cross sectional view showing a cup placed into a cup sleeve and placed into a prepared acetabulum with a mechanical interlock released in accordance with the present invention.

DETAILED DESCRIPTION OF THE INVENTION

As described above, the present invention is applicable to orthopaedic surgical procedures for Kinematic Restoration, spinal interbody fusion, vertebral compression fracture reduction and realignment osteotomy. In one embodiment of the present invention, the system is comprised of:
- an implant—in this embodiment the implant is an acetabular cup,
- a distracter—in this embodiment the distracter is a cup inserter and specifically the stage II piston and cylinder,
- a sleeve—in this embodiment the sleeve is a cup sleeve,
- optionally, an alignment guide—in this embodiment the alignment guide is a cup alignment guide,
- optionally, a surgical navigational tracker—in this embodiment the surgical navigational tracker is a cup navigational tracker,
- optionally, a bone displacer—in this embodiment the bone displacer is the stage I piston and cylinder.

Figure 1:
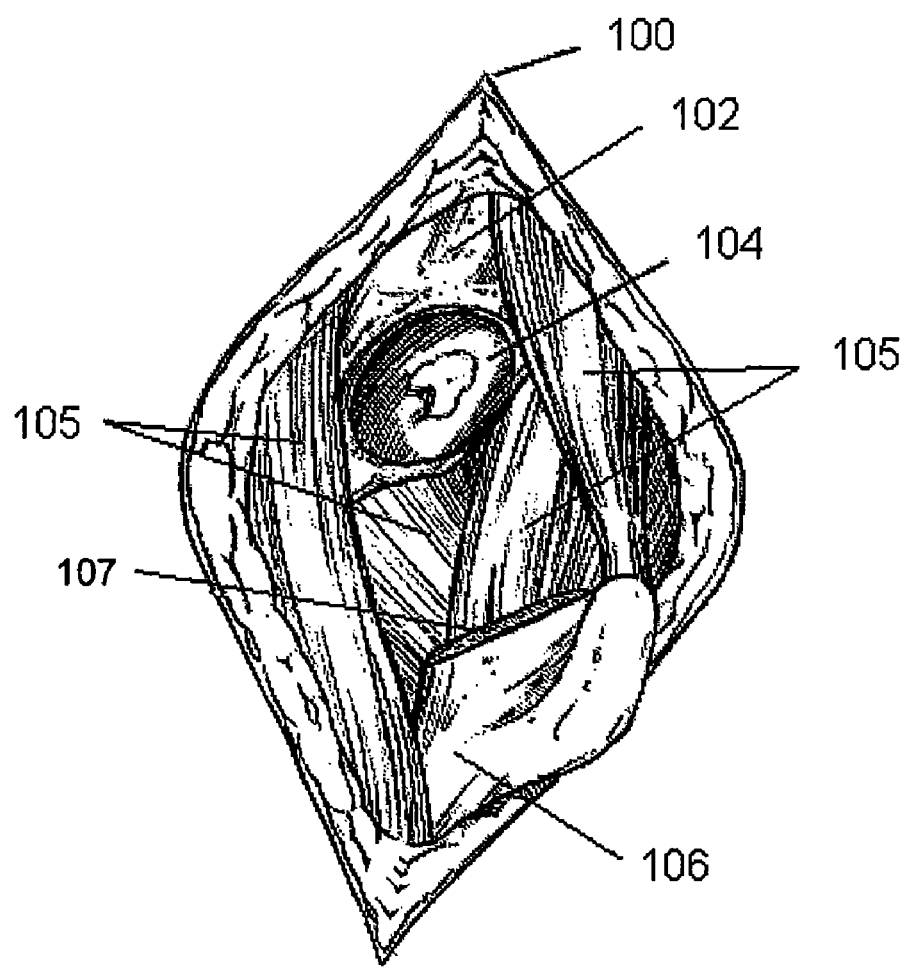
FIG. 1 is a perspective view of the surgical incision through which the present invention is structured to be used.

Referring to FIG. 1, there is depicted a surgical incision 100 for a less invasive total hip arthroplasty. The muscles and soft tissues spanning the hip joint are exposed and either bluntly dissected along muscle fibers or separated along muscle boundaries. Optionally, select muscles may be taken down to increase surgical exposure and access to the hip joint. Anatomy of interest to this embodiment of the invention includes the pelvis 102, the acetabulum 104, the femur 108, the joint capsule (not shown) and the muscles 105 and ligaments spanning the hip joint. The femoral head is resected at the base of the femoral neck 108 as shown in FIG. 1 to provide access to the medullary canal to prepare the canal to receive a femoral hip stem. In total hip arthroplasty, the articular surfaces of the proximal femur and the acetabulum are resurfaced. In general, after resecting the femoral head, the femur is prepared by reaming and broaching to prepare the femoral canal to receive a hip stem implant and femoral head implant there on. Alternatively, the femoral head may be sculpted to receive a resurfacing implant structured to fit over the prepared femoral head, this representing another embodiment of the present invention to place an implant onto a prepared bone surface. The acetabulum is generally prepared by reaming a hemispherical cavity to receive an acetabular cup.

Figure 2A:
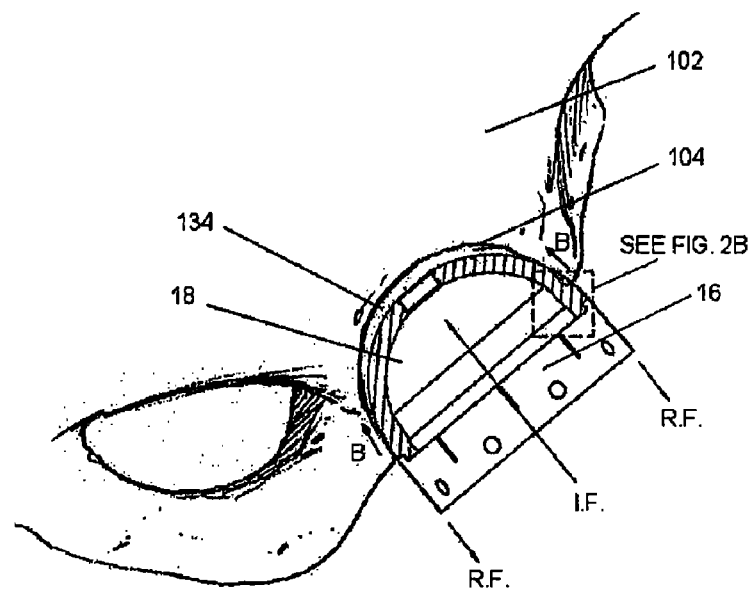
FIG. 2A is an illustration of a cup placed into a sleeve and placed into a prepared acetabulum in accordance with the present invention.
Figure 2B:
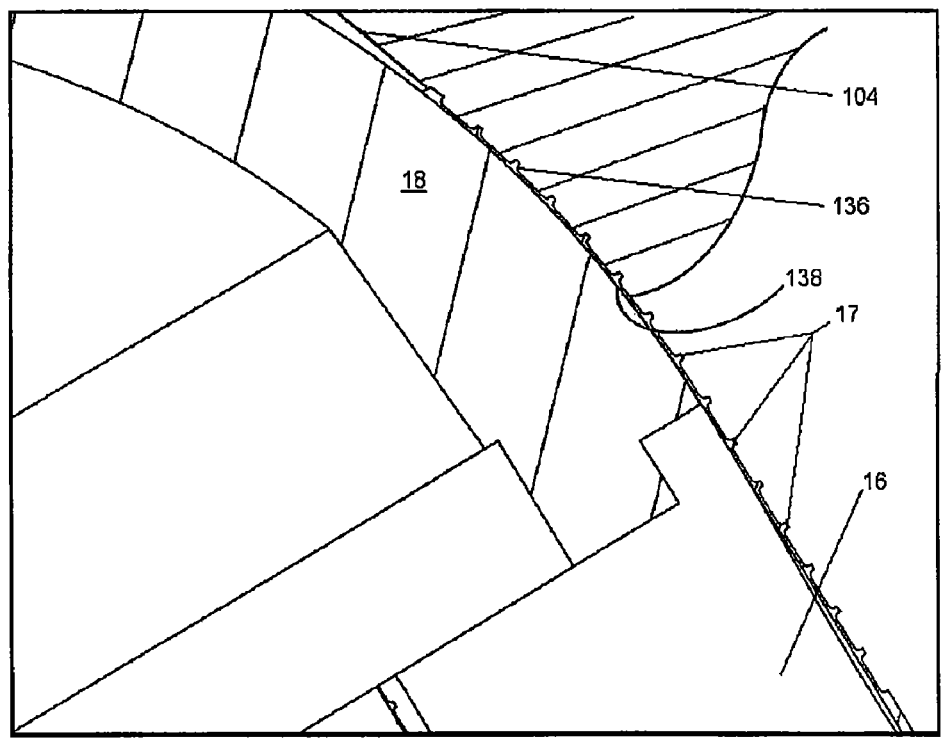
FIG. 2B is a cross sectional detailed view of FIG. 2A showing a cup placed into a cup sleeve and placed into a prepared acetabulum in accordance with the present invention.

Referring to FIG. 2A, the cup sleeve 16 interposes the cup 18 and the acetabulum 104. The cup 18 size is selected to provide a press-fit within the prepared acetabulum 104 and the cup sleeve 16 size is selected to match the cup 18 size. Alternatively, a cup sleeve 16 may be structured to accommodate multiple cup sizes. The cup inserter, described in detail below, provides an insertion force IF to the cup 18 that is reacted by the cup sleeve 16 by a reaction force RF around the distal circumference of the cup sleeve. Now referring to FIG. 2B, the cup sleeve 16 to acetabulum 104 interface 136 is structured to provide a higher engagement force than the engagement force at the cup sleeve 16 and cup 18 interface 138. The cup sleeve 16 surface at the sleeve-bone interface 136 is structured with circumferential ridges 17 to provide a mechanical interlock and an engagement force higher than that of the sleeve-implant interface 138 in which the sleeve surface is smooth. The ridges may be machined into the sleeve. Alternatively, the ridges may be chemically milled into the sleeve, or formed into the sleeve by a stamping process. Alternatively, the sleeve surface at the sleeve-bone interface 136 may be structured with a roughened texture as may be created by grit blasting, machining, chemical etching or formed into the sleeve by a stamping process.

Alternatively, the cup sleeve 16 surface at the sleeve-bone interface 136 may be structured to provide a releasable mechanical interlock. Referring to FIG. 3, the cup sleeve 16 may be structured with a circumferential ridge 133 around the proximal edge that engages the acetabulum 104. A sliding spacer 131 is interposed between the cup sleeve 16 and cup 18 to hold the ridge 133 in an extended position to engage the acetabulum 104. The sliding spacer 131 is pulled distally by the surgeon grabbing the sliding spacer 131 with a forceps. As shown in FIG. 4, when the sliding spacer 131 is pulled from underneath the circumferential ridge 133, the ridge 133 pulls away from the acetabulum 104 releasing the cup sleeve 16 to slide from the cup 18 and acetabulum 104 interface. Alternatively, the ridge 133 may be intermittent to provide equally spaced tabs around the circumference of the proximal edge of the cup sleeve 16 to engage the acetabulum 104.

Figure 5:
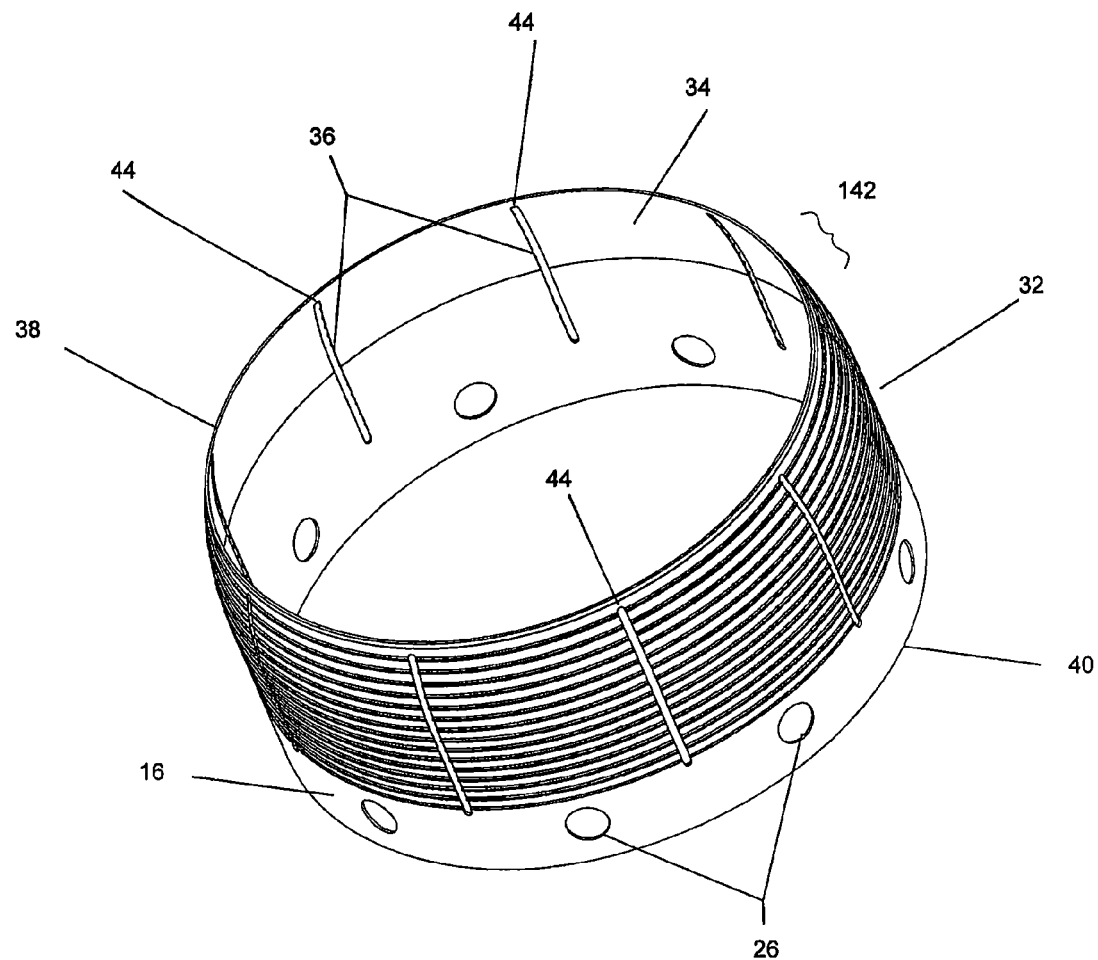
FIG. 5 is a perspective view of a sleeve in accordance with the present invention.

Now referring to FIG. 5, the body of the cup sleeve 16 is formed with a spherical closing 142 of the proximal edge 38. The longitudinal serrations 36 equally spaced around the cup sleeve 16 provide relief in the cup sleeve 16 as the cup displaces proximally through the cup sleeve 16. The serrations 36 are positioned relatively close to the proximal edge 38 to provide a lip 44 between each serration 36 and the proximal edge 38, this lip 44 structured to provide constraint to hold the cup in the cup sleeve while the surgeon handles the cup inserter and cup to place the construct into the surgical site. The lip 44 then fracturing as the cup is advanced into the acetabulum to allow the cup to pass through the cup sleeve 16 as described in greater detail below. The perforations 26 evenly spaced around the distal aspect of the cup sleeve 16 are structured to provide a releasable pinned connection with the cup inserter as described in greater detail below. Alternatively, the perforations 26 may be structured to provide a pinned connection with the cup inserter.

The body of the cup sleeve 16 may be formed by deep drawing a metal into the shape of the cup sleeve 16, then truncating the formed can to open the proximal end of the cup sleeve 16 and trimming the distal end 40 of the formed can. Alternatively, the cup sleeve 16 body may be machined. The longitudinal serrations 36 and perforations 26 can be die cut into the cup sleeve 16. Alternatively, the longitudinal serrations 36 and perforations 26 may be laser cut or die stamped into the cup sleeve.

Figure 6:
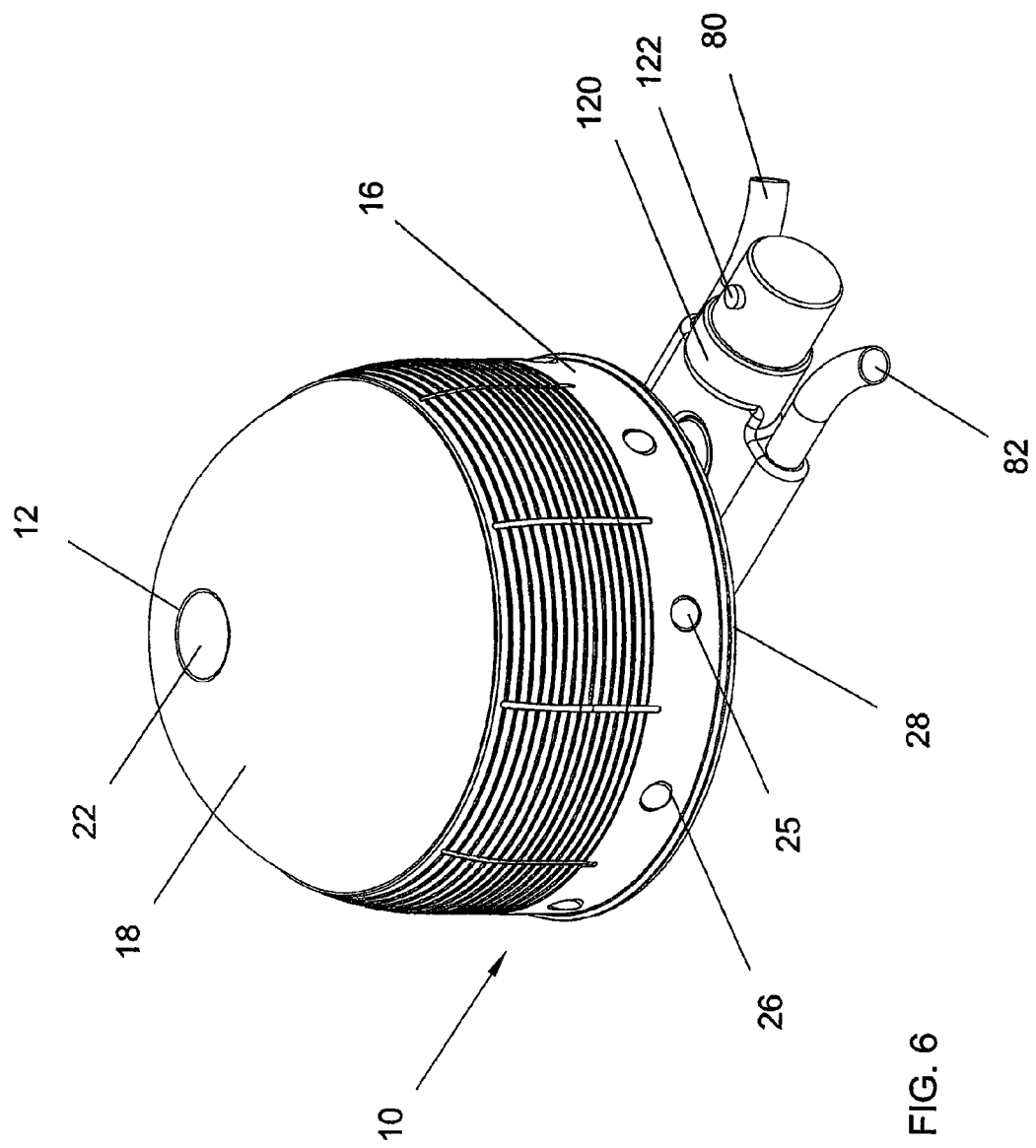
FIG. 6 is a top perspective view of a cup inserter in accordance with the present invention.
Figure 7:
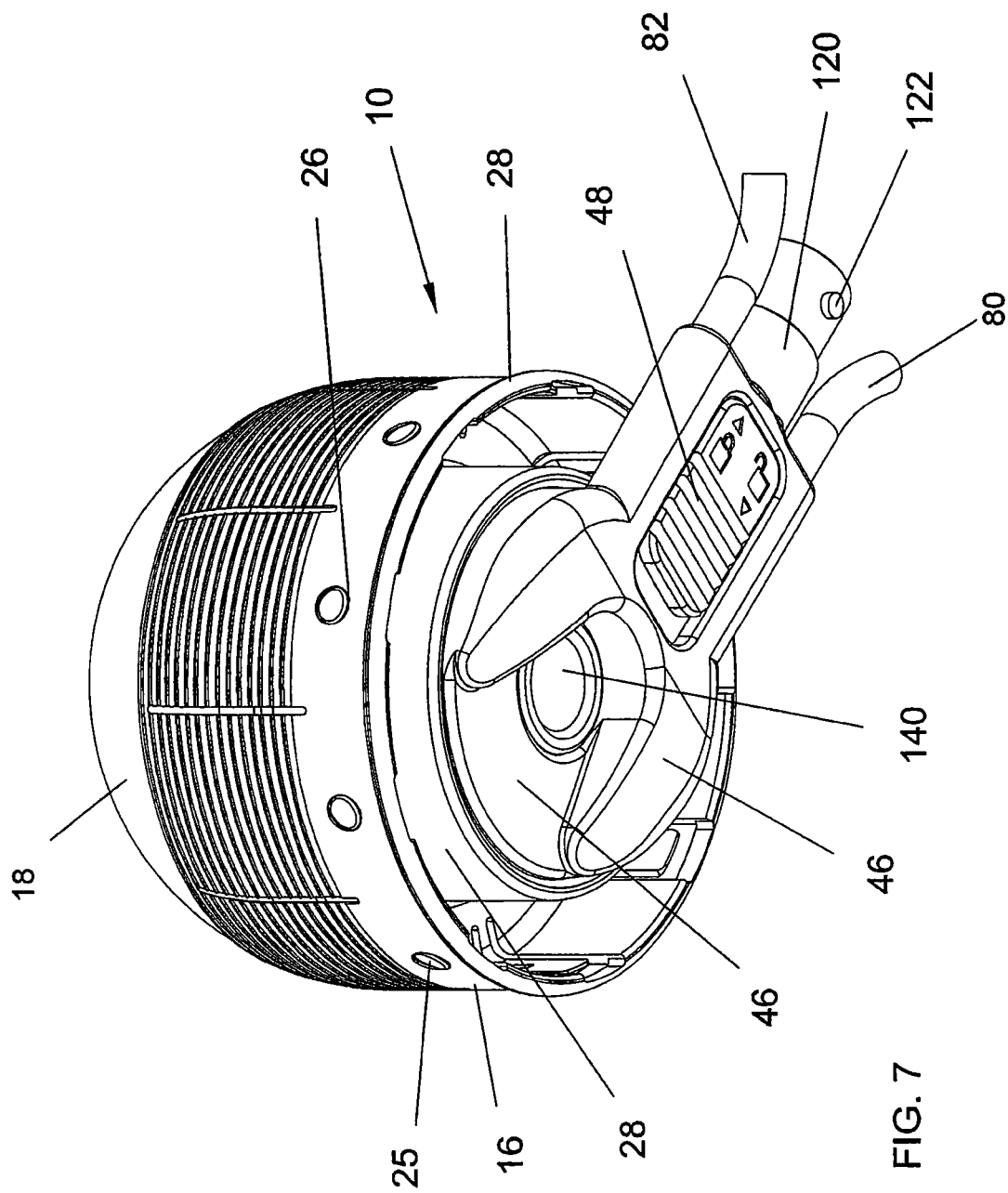
FIG. 7 is bottom perspective view of the cup inserter in accordance with the present invention.

Referring now to FIGS. 6 and 7 which illustrate an assembly of the present invention, the cup 18 is held within the cup sleeve 16. The cup sleeve 16 is structured to attach to the adapter ring 28 with releasable pinned interlocks that engage perforations 37 in the cup sleeve 16. In one embodiment, the present invention includes a distracter and a bone displacer. Hydraulic pressure to activate the distracter is provide via a tube 82 which is ported to the stage II piston and cylinder described in detail below. Hydraulic pressure to activate the bone displacer is provided via a tube 80 which is ported to the stage I piston 140 and cylinder described in detail below. The cup inserter 10 is structured to attachably receive a handle to a boss 120 via two bayonet mounting tabs 122. The manifold cap 46 is structured to be assembled and disassembled with the adapter ring 28 through a threaded connection described below. This threaded connection is locked from loosening during the surgical procedure by a mechanical interlock activated by a manifold lock 48 on the distal surface of the manifold cap 46.

Figure 8:
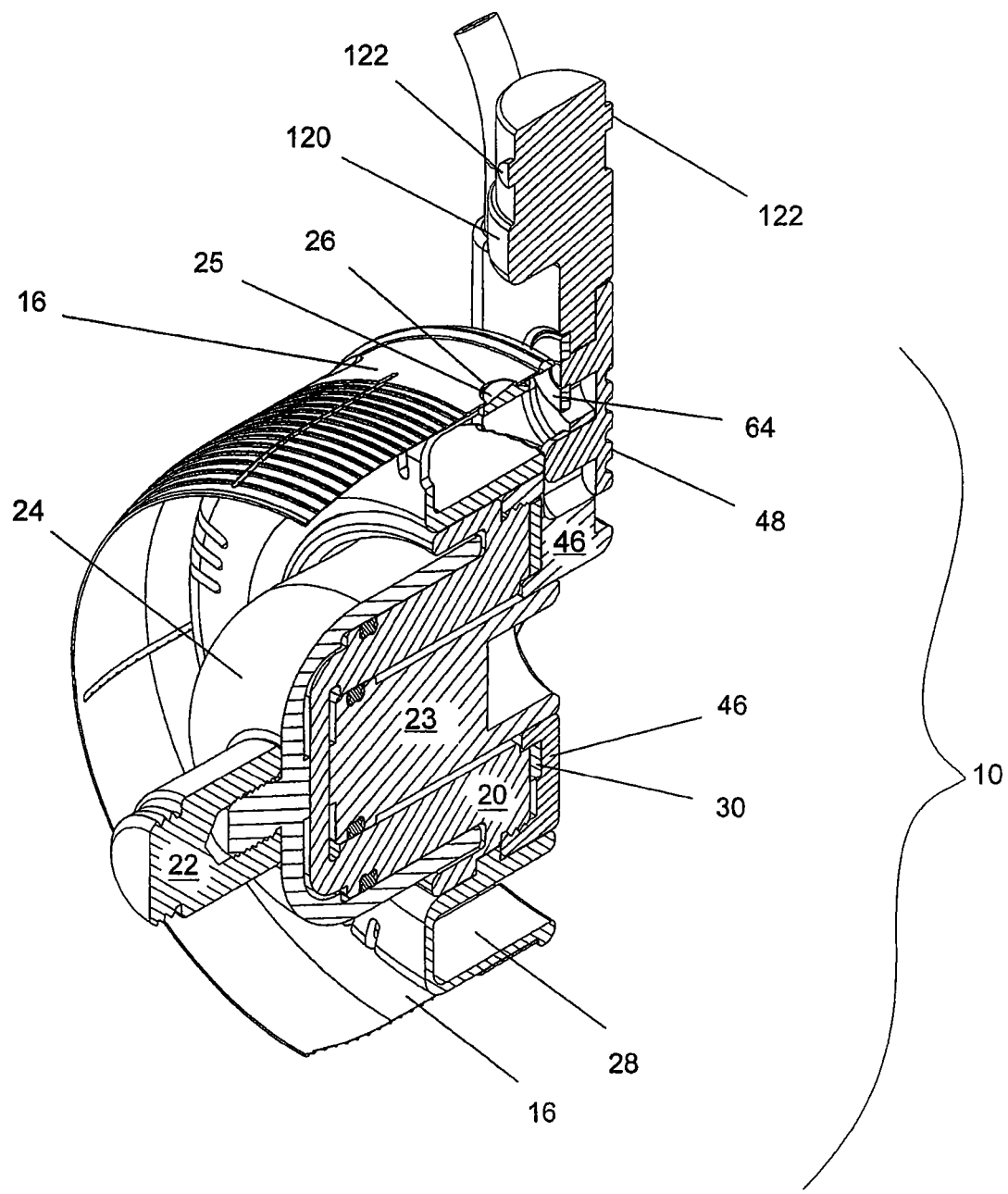
FIG. 8 is a perspective cross sectional view of the cup inserter of the present invention.
Figure 9:
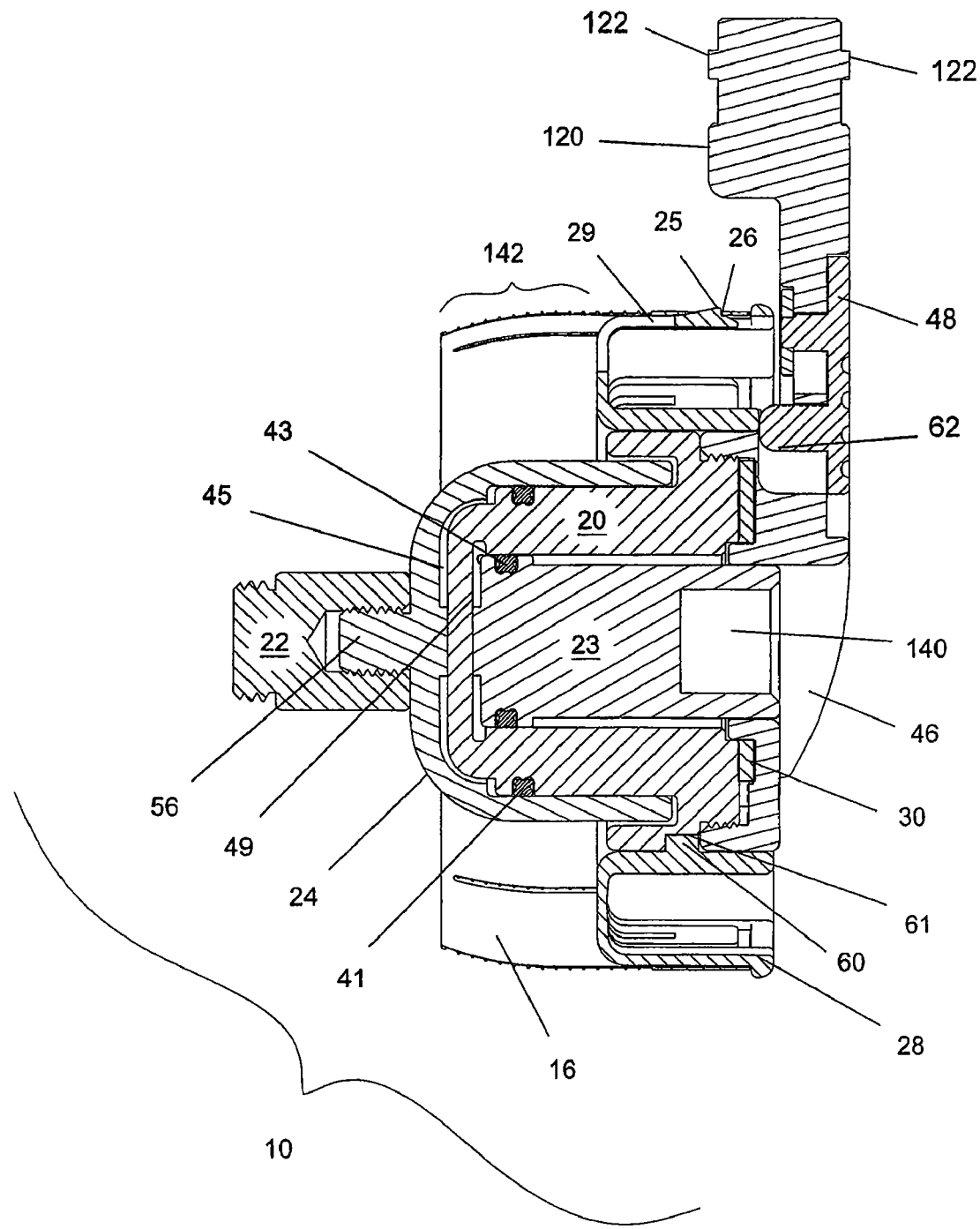
FIG. 9 is a cross sectional view of the cup inserter of the present invention.

The operation of the cup inserter 10 is easiest to describe when referring to FIGS. 8 and 9 which are cross sectional views of the cup inserter 10 without a cup, but with a cup sleeve 16 illustrated. As described above, first hydraulic pressure supply is used to actuate a distracter structured within the cup inserter 10 and a second hydraulic pressure supply is used to actuate a bone displacer structured within the cup inserter 10. The distracter is comprised of manifold 20 and stage II piston 24 structured to provide a piston and cylinder mechanism that when pressurized displaces the cup relative to the cup sleeve 16. Hydraulic pressure is introduced via tube 82 described above and ported to the stage II cylinder 45. An o-ring 41 provides a pressure seal for the stage II piston 24 and manifold 20. The manifold 20 engages the adapter ring 28 through a mechanical interlock structured by tabs 60 on the inner diameter of the adapter ring 26 slidably fitting into receiving pockets 61 in the outside diameter of the manifold 20.

The manifold 20 attaches to the cup sleeve 16 via a releasable pinned interlock formed by a cantilever beam 29 and boss 25 in the adaptor ring 28. Multiple cantilever beam 29 and boss 25 interlocks are equally spaced around the adaptor ring 28 and the number varies with the size of the adaptor ring 28 as structured to attached to various sizes of the cup sleeve 16.

The cantilever beam 29 is deflected inward by applying force to the boss 25 thereby releasing the cup sleeve. The proximal edge of each boss 25 is beveled to allow the cup sleeve to slide over the boss 25 and depress the cantilever beam 29 during assembly of the cup sleeve 16 onto the adaptor ring 28. Extending from the proximal surface of the stage II piston 20 is a treaded connector 56 structured to attach an adapter post 22. Adapter posts 22 are provided for each cup size. The proximal end of the adapter post 22 is structured with a treaded connector 22 to attach to the cup. Alternatively, the proximal end of the adapter post 22 may be structured with a boss that slidably fits into a apical hole in the cup.

Once assembled, the cup inserter 10 is locked in an assembled position by the manifold lock 48 and boss 62 that slidably engages scallops 88 on the distal inner surface of the adapter ring 28. Releasing the manifold lock 48 allows the manifold 20 to be unthreaded from the manifold cap 46 and disassembly of the cup inserter 10.

The bone displacer is comprised of the stage I piston 26 and the cylinder within the manifold 20. An o-ring 43 provide a pressure seal between the stage I piston 26 and the cylinder within the manifold 20. The distal end of the stage I piston 26 is structured with a bore 140 to slidably receive the post of a femoral broach to support the cup inserter 10 when in use within the joint cavity. Alternatively, the cup inserter may be used independently without attachment to a broach or support by the femur.

Figure 10A:
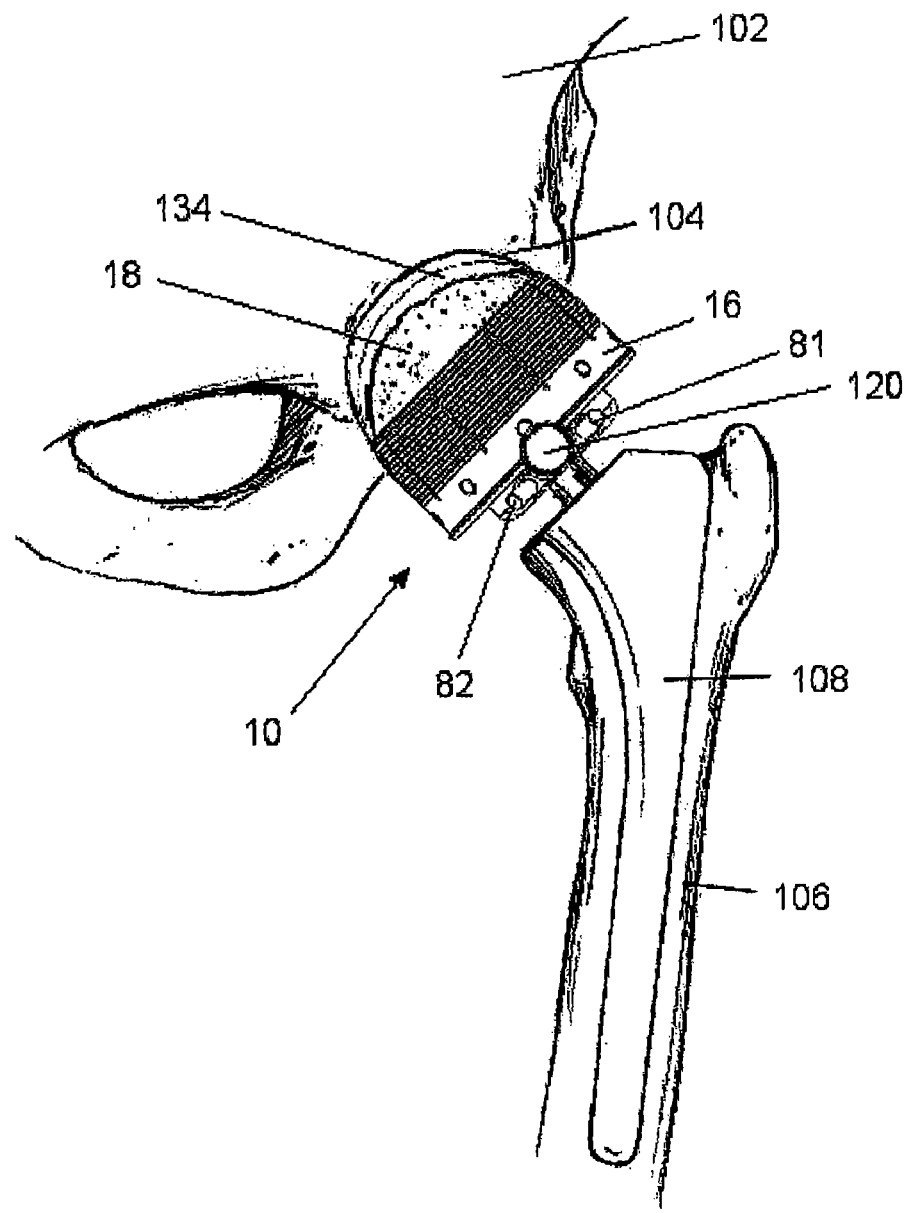
FIG. 10A is a side view of a cup inserter aligned for placement of an acetabular cup in accordance with the present invention.
Figure 10B:
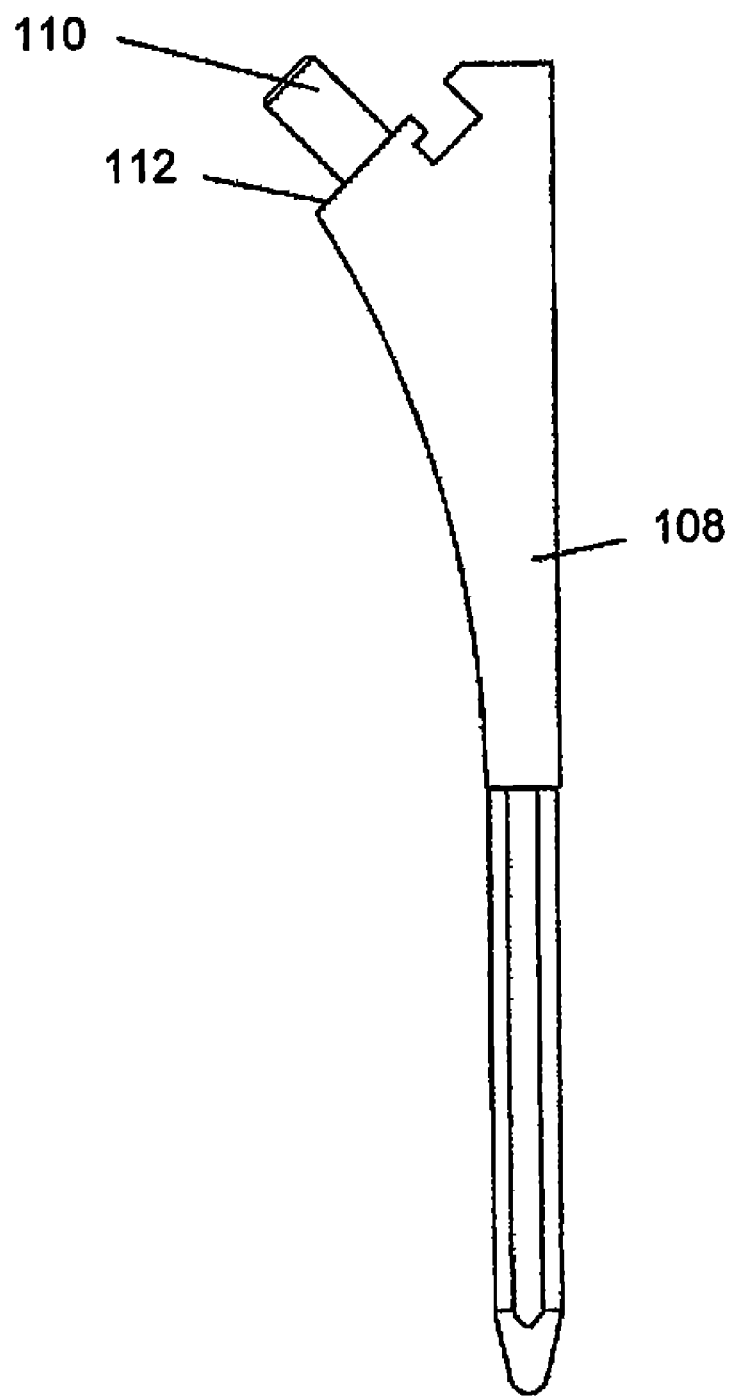
FIG. 10B is a side view of a femoral broach in accordance with the present invention.

Turning now to a description of the surgical procedure in which the cup inserter 10 is used to place a cup 18. The acetabulum 104 and proximal femur have been surgically prepared as described above. The femoral broach that was used to prepare the proximal femur is left in place to support the cup inserter 10. Starting with FIG. 10A, the cup inserter 10 and bone displacer are fully retracted. A cup 18 size is selected to provide a press-fit with the prepared acetabulum 104 and assembled with the cup inserter 10 and cup sleeve 16. The cup handle is assembled to the cup inserter 10 onto boss 120 as described in detail below. Next, the cup inserter 10 is placed onto the broach post 110, as can be seen in FIG. 10B, and the hip is reduced to place the cup 18 into the acetabulum 104. Alternatively, the cup inserter 10 may be attached directly to the femur with screws, pins or other suitable mounting structure. Alternatively, the cup inserter 10 may be supported by the proximal femur without mechanical attachment thereto. Alternatively, the cup inserter 10 may be structured to place the cup without the cup inserter 10 attached to or supported by the femur.

It should be noted that due to the press-fit interference between the cup 18 and acetabulum 104, the cup 18 is supported by the distal circumference of the acetabulum leaving a gap 134 apically between the cup 18 and acetabulum 104. The stage I piston 26 is advanced by applying pressure with a syringe pump until the joint capsule is tensioned appropriately and the cup sleeve 16 engages the acetabulum 104. The stage II piston 24 is advanced to provide an insertion force to the cup 18. The insertion force is reacted through the sleeve 16 by a reaction force carried by the adaptor ring 28 attached to the cup sleeve 16; hence, the stage II piston 24 is structured to provide a distraction force between the cup 18 and the sleeve 16. The sleeve 16 is held in place within the acetabulum by the higher engagement force at the sleeve-acetabulum interface, than that of the sleeve-cup interface as previously described. The cup 18 slides relative to the sleeve 116 until the gap apical 134 between the cup 18 and acetabulum 104 is closed. At which point the distraction force provided by the stage II piston 24 pulls the sleeve 16 from the acetabulum 104 by overcoming the frictional force at the sleeve-acetabulum interface as previously described.

Figure 11:
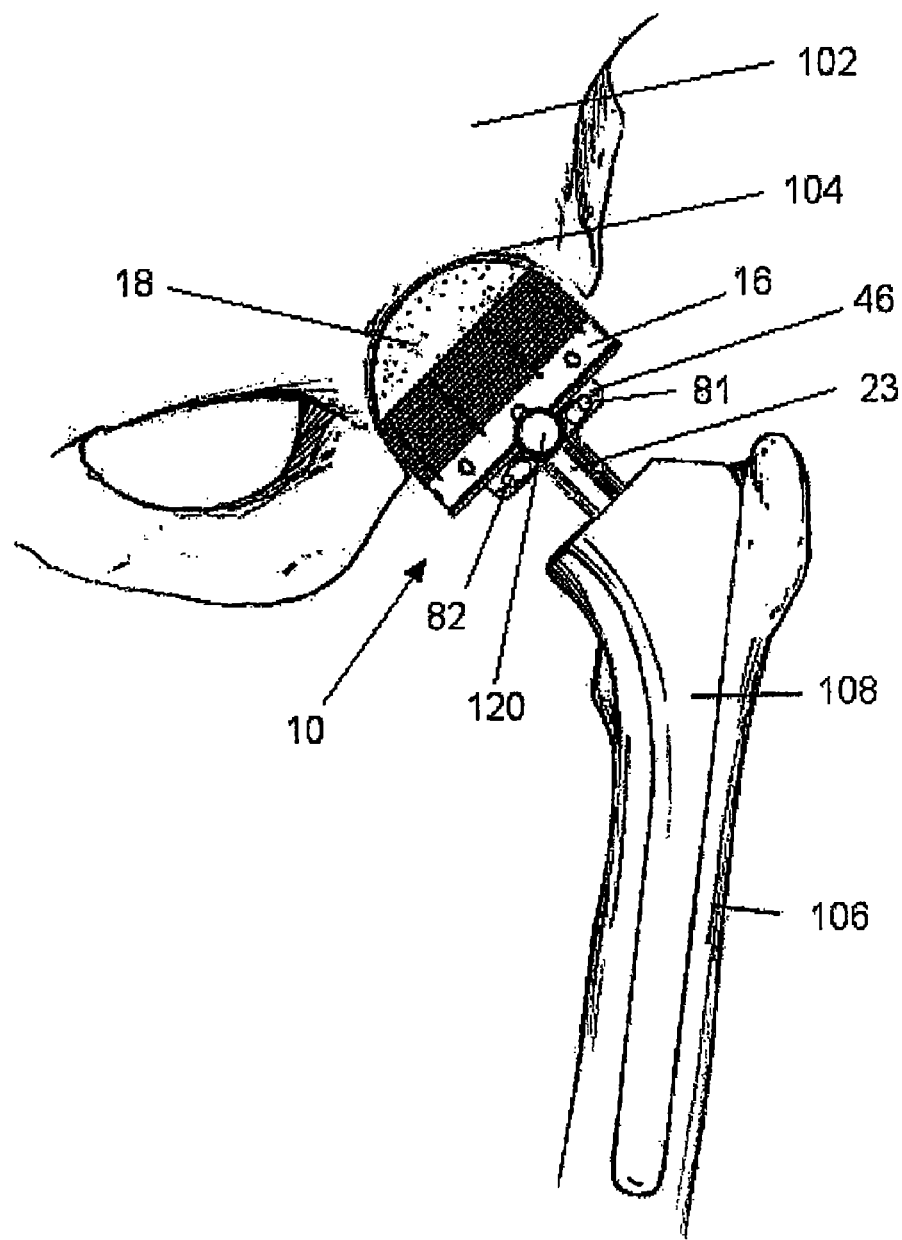
FIG. 11 is a side view of a cup inserter inserting an acetabular cup in accordance with the present invention.
Figure 12:
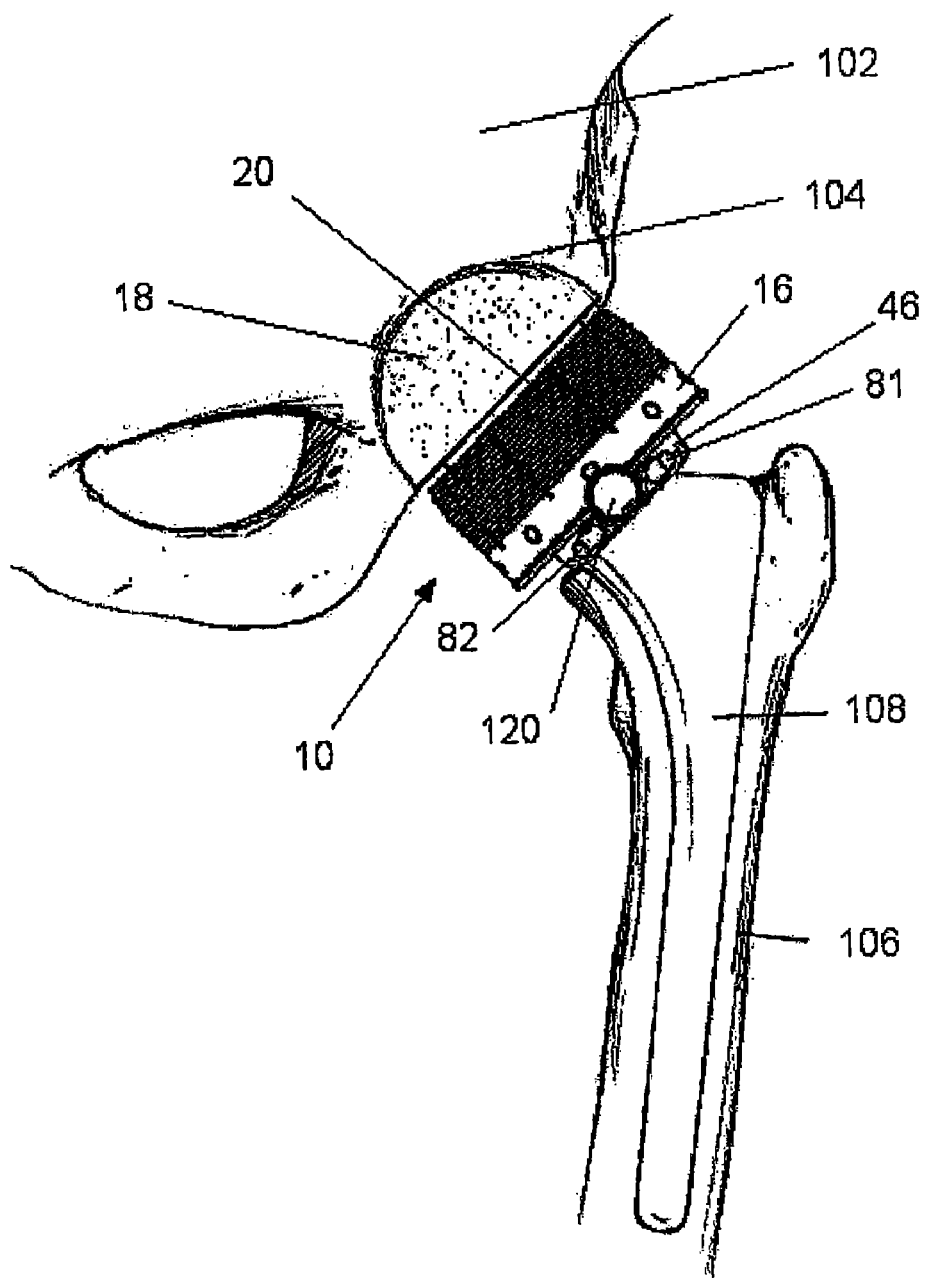
FIG. 12 is a side view of a cup inserter extracting a sleeve in accordance with the present invention.

Referring now to FIG. 11, as the stage II piston deploys to seat the cup 18, the stage I piston is adjusted to maintain distraction of the joint capsule and displace the femur. Now referring to FIG. 12, after the cup 18 is fully seated in the acetabulum 104, the stage II piston 24 continues to pull the sleeve 16 from the cup-acetabulum interface until the sleeve 16 is fully removed. At this point the manifold 20 is free from the stage II piston 24 and the sleeve 16, adaptor ring 28, manifold 20 and manifold cap 46 assembly are removed from the hip joint cavity by orienting the femur away from the acetabulum and removing these components from the broach post 110. The stage II piston 24 and adaptor post 22 are then removed from the cup 18.

Figure 13A:
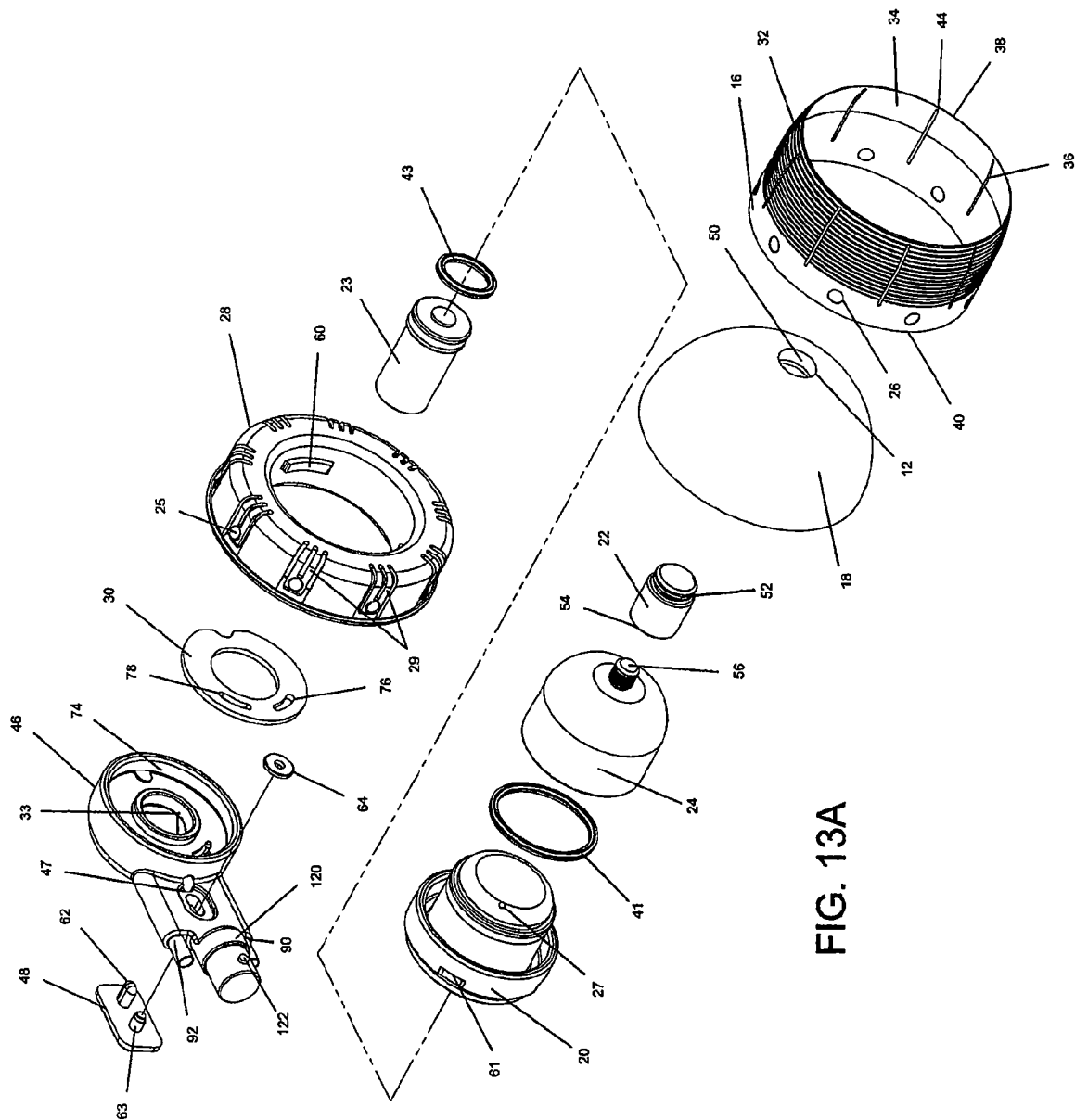
FIG. 13a is an exploded view of the cup inserter in accordance with the present invention.
Figure 13B:
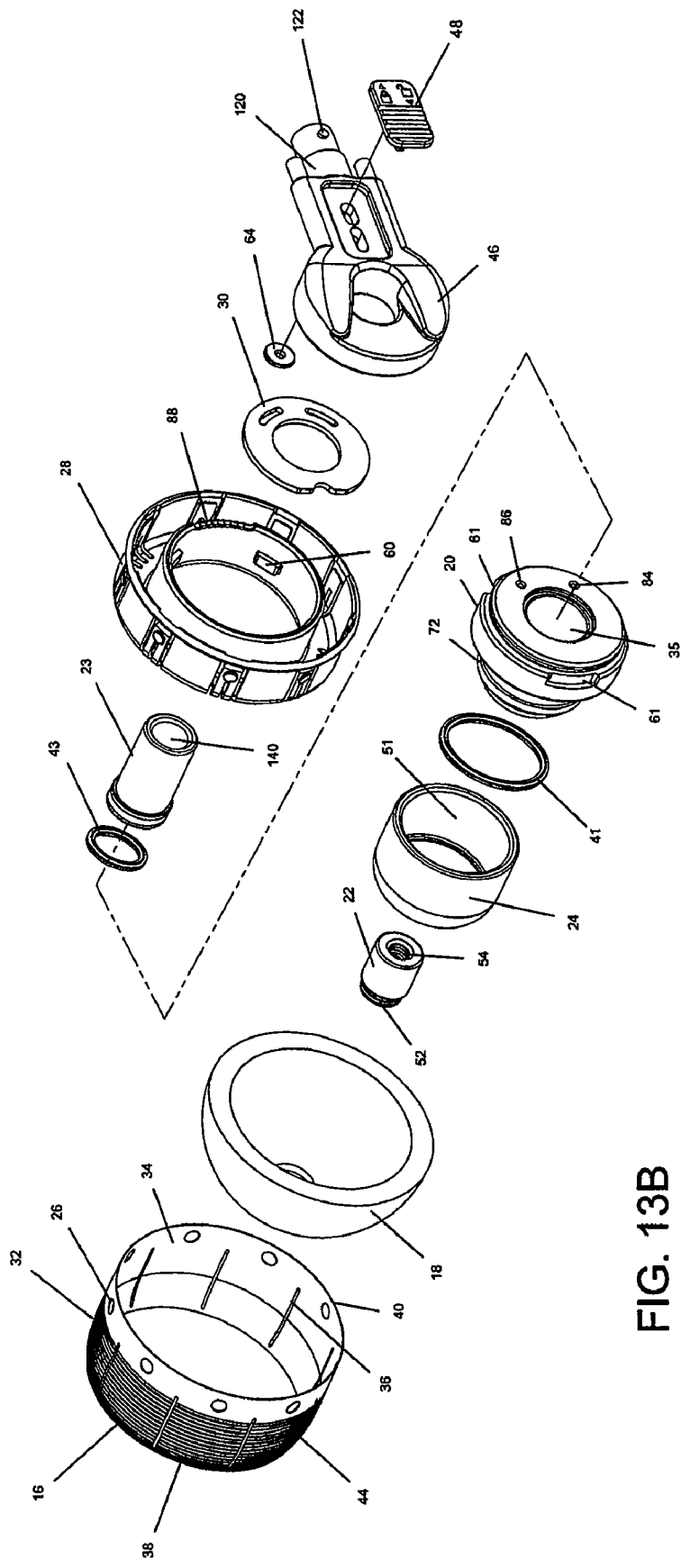
FIG. 13b is another exploded view of the cup inserter in accordance with the present invention.

Given the numerous parts making up the cup inserter 10, it is beneficial to briefly list the parts as shown in exploded views. Referring to FIGS. 13a and 13b, the cup sleeve 16, the cup 18, the adapter post 22, the stage II piston 24, the manifold 20 with o-ring 41 assembled, the stage I piston with o-ring 43 assembled, the adapter ring 28, the manifold gasket 30, the manifold cap 46, the manifold lock 48 and the manifold retainer 64. It is also beneficial to briefly describe the fluid pathways for the distracter, driven by stage II, and the bone displacer, driven by stage I, configurations within the cup inserter 10. Starting with the pressure supply, a first and a second syringe pump (not shown) are used to provide hydraulic pressure to drive stage I and stage II pistons. Each syringe pump is filled with sterile saline solution. The first syringe pump is connected to stage I via tube 80 and the second syringe pump is connected to stage II via tube 82. The fluid pathway for stage I is tube 80-manifold cap 46 port 90-gasket 30 port 76-manifold 20 port 84-leading to manifold 20 internal cylinder 35. The fluid pathway for stage II is tube 82-manifold cap 46 port 92-gasket 30 port 78-manifold 20 port 86-leading to manifold 20 external cylinder 27.

Figure 14:
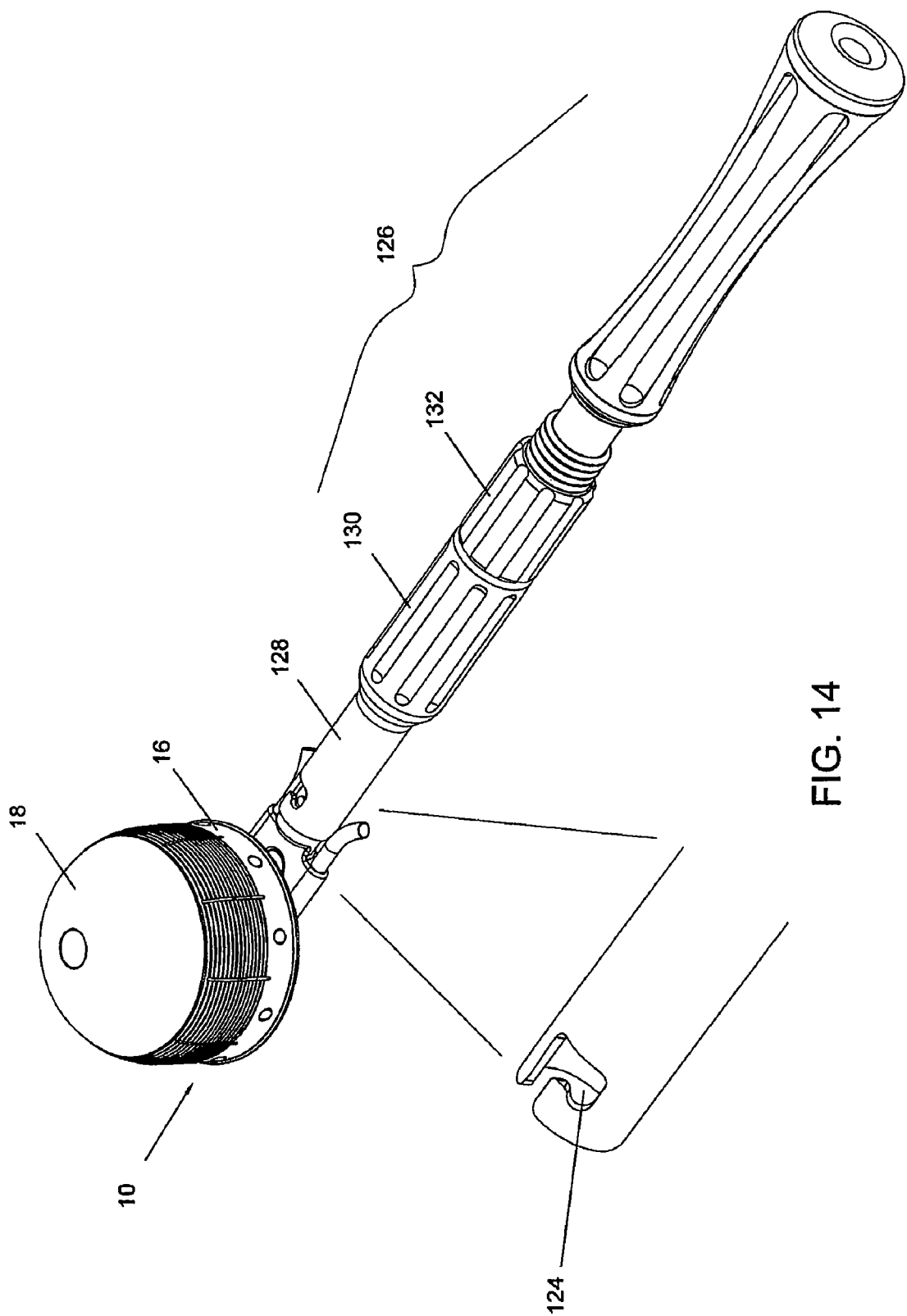
FIG. 14 is a perspective view of a cup inserter and handle in accordance with the present invention.

Referring to FIG. 14, in another embodiment in accordance with the present invention, the cup inserter 10 is attached to a handle 126 such that a surgeon places cup inserter 10 and cup 18 directly into the acetabulum and holds sleeve 16 in contact with supporting bone. The handle 126 structured to slidably receive the manifold cap attachment boss 120 with opposing bayonet bosses 122 to engage receiving bayonet openings 124. The lock nut 130 is structured to secure the bayonet bosses 122 within the receiving bayonet openings 124, and the clinch nut 132 structured to lock the lock nut 130 in place. Alternatively, the cup inserter 10 may be structured to attach to or be supported by the femur directly or indirectly as described above. The stage II piston 24 is extended to push cup 18 along sleeve 16 and into the acetabulum. The frictional force between sleeve 16 and supporting bone holds sleeve 16 in position relative to the supporting bone until inserter cup 10 is seated in supporting bone. After seating, cup inserter 10 is in proper position and additional pulling force to sleeve 16 slides sleeve 16 from the cup-bone interface. This is continued until sleeve 16 is free of the interface at which time cup inserter 10 and sleeve 16 are removed from the joint cavity and the surgical procedure is completed.

Figure 15:
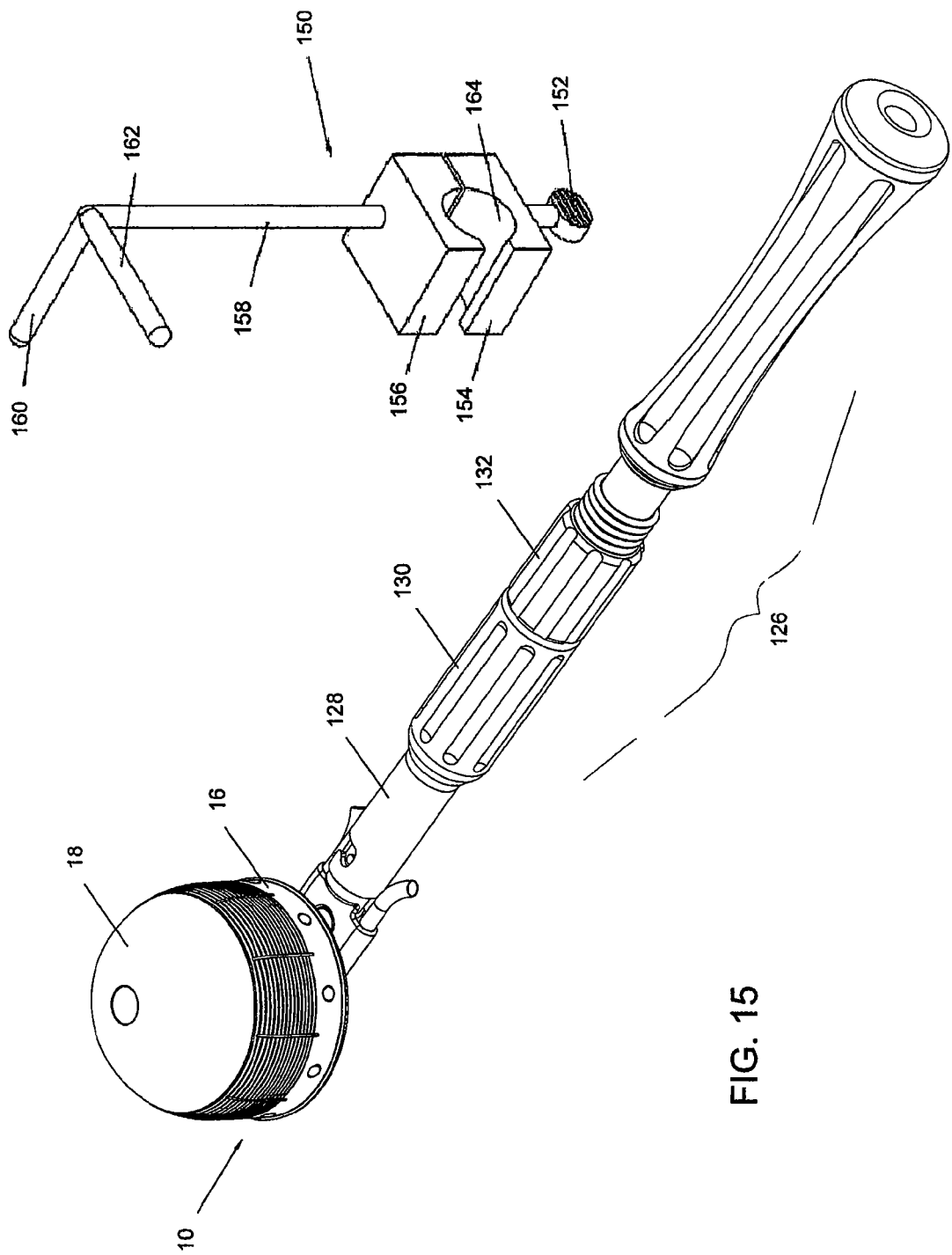
FIG. 15 is a perspective view of a cup inserter, handle and alignment guide in accordance with the present invention.

Optionally, the cup inserter 10 and handle 126 may be structured for attachment of an alignment guide. Referring to FIG. 15, an alignment guide 150 with an alignment rod 162 structured to indicate cup inclination and alignment rod 160 structured to indicate cup anteversion relative to the axis of the torso may be used to check alignment of the cup 18 by attaching the alignment guide 150 to handle 126, such attachment structured as a channel 164 in the upper base 156 and lower base 154 of the alignment guide 150 that slidably fits over the handle 126 via channel 164 and clamps to the handle 126 thumb screw 152 to stabilize the alignment guide 150 in proper alignment relative to the cup inserter 10 and handle 126. Alternatively, the alignment guide may be attached to the handle 126 by threaded fasteners passed through clearance receiving holes in the upper base 156 and threaded into threaded receiving holes in the handle 126.

Figure 16:
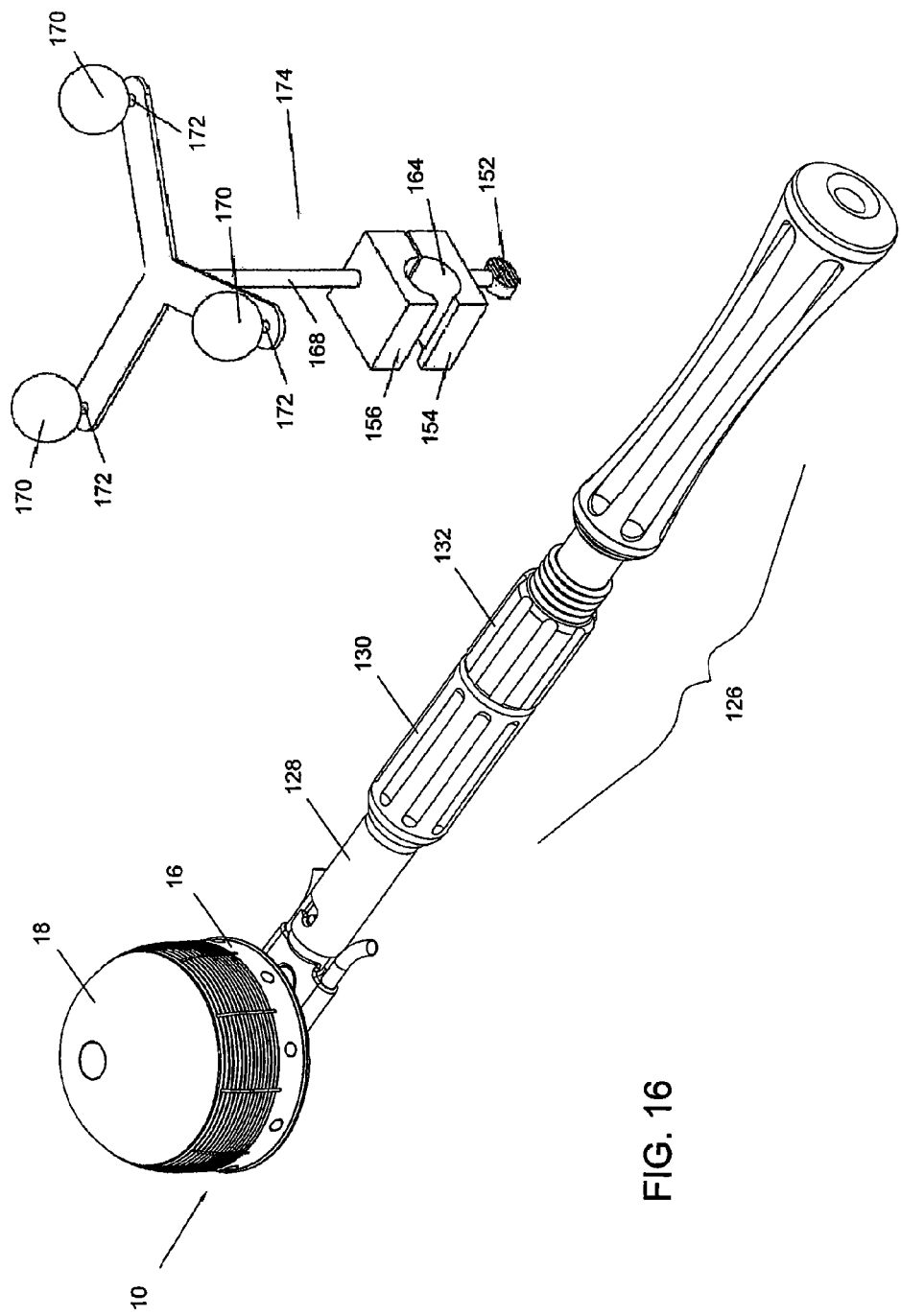
FIG. 16 is a perspective view of a cup inserter, handle and surgical navigational tracker in accordance with the present invention.

Optionally, the cup inserter 10 and handle 126 may be structured for attachment of a surgical navigational tracker for use with a surgical navigational system. Referring to FIG. 16, a surgical navigational tracker 166 with three reflective spheres 170 supported on a frame 168 and an upper base 156 and lower base 154 of the alignment guide 150 that slidably fits over the handle 126 via channel 164 and clamps to the handle 126 thumb screw 152 to stabilize the alignment guide 150 in proper alignment relative to the cup inserter 10 and handle 126. Alternatively, the surgical navigational tracker 166 may be attached to the alignment guide 150 to handle 126 by threaded fasteners passed through clearance receiving holes in the upper base 156 and threaded into threaded receiving holes in the handle 126. Cup 18 alignment is checked with the a surgical navigational tracker 166 attached to the cup inserter 10 and handle 126. The surgical navigational system will measure cup 18 inclination and anteversion and provide a report to the surgeon. Alternatively, the alignment guide 150 and the surgical navigational tracker 166 may be structured for attachment to the cup inserter 10 and handle 126 with "T" slots; dovetail locks; cylindrical interlocks; button interlocks; spherical interlocks; or a combination of these, or other connecting means used to connect two or more parts.

While this disclosure covers placing a cup into the acetabulum, the present invention is applicable to orthopaedic surgical procedures for Kinematic Restoration, spinal interbody fusion, vertebral compression fracture reduction and realignment osteotomy.

It is contemplated that features disclosed in this application can be mixed and matched to suit particular circumstances. Various other modifications and changes will be apparent to those of ordinary skill in the art without departing from the spirit and scope of the present invention. Accordingly, reference should be made to the claims to determine the scope of the present invention.

What is claimed is:

1. A system for seating an implant into a first bone or an adjacent second bone comprising:
    an implant;
    an instrument for seating said implant into a first bone or an adjacent second bone, said instrument including a distracter and a sleeve coupled to said distracter, said distracter in communication with at least one of said implant, said first bone or said second bone,
    said sleeve structured to interpose said implant and said first bone or adjacent second bone, the sleeve having a sleeve-to-implant interface and a sleeve-to-bone interface, said sleeve structured to releasably cover at least a portion of said implant and structured to be releasably removed from said implant to bone interface as said sleeve pulls said first bone or adjacent second bone to said implant upon advancing and seating of the implant into the first bone or adjacent second bone without removing said implant from said implant to bone interface, the sleeve having an engagement force on a surface in communication with said implant that is different than a surface in communication with said first bone or adjacent second bone, said differential engagement force structured to preferentially move the implant into said first or adjacent second bone wherein said distracter is structured to displace said sleeve relative to said implant, or displace said implant relative to said sleeve, or displace said implant relative to said first or second bone.

2. The system of claim 1 further comprising a bone displacer in communication with said distracter; said bone displacer structured to displace the first bone away from the second bone.

3. The system of claim 1 wherein the sleeve comprises a truncated sphere.

4. The sleeve of claim 3 further comprising a plurality of longitudinal serrations having first and second ends, each of said plurality of serrations in spaced apart relationship on said sleeve.

5. The sleeve of claim 4 further comprising a lip extending circumferentially around the truncated sphere at one end thereof.

6. The sleeve of claim 5 wherein said first end of each of said plurality of serrations is proximate said lip.

7. The sleeve of claim 6 wherein said plurality of serrations allow said sleeve to substantially conform to the shape and size of said implant.

8. The sleeve of claim 6 wherein said plurality of serrations allow said lip to break when said implant is seated.

9. The system of claim 3 wherein said sleeve further comprises a plurality of ridges extending circumferentially around said truncated sphere, wherein the surface of said plurality of ridges is grit blast, chemically etched, corrugated or patterned.

10. The sleeve of claim 5 further comprising a plurality of perforations positioned in spaced apart relationship on an end of said truncated sphere opposite said lip.

11. The system of claim 1 further comprising a cup inserter operably connected to said sleeve, said cup inserter including a receiving hole for slidably receiving a broach post mounted to a femoral broach.

12. The system of claim 1 wherein said sleeve comprises at least one material selected from the group consisting of cobalt-chromium alloy, stainless steel, titanium, titanium alloys, Nitinol urethane, polyethylene, expanded polyethylene, nylon, and woven fabric materials.

13. The system of claim 1 further comprising a plurality of sleeves.

14. The system of claim 1 further comprising an alignment guide operably coupled with at least one of said sleeve, said implant, said first bone or said second bone.

15. The system of claim 1 further comprising a surgical tracker operably coupled with at least one of said sleeve, said implant, said first bone or said second bone.

16. The system of claim 1 wherein said engagement force is lower on the surface in communication with said implant than the surface in communication with said first bone or adjacent second bone.

17. A system for seating an implant into a first bone or adjacent second bone comprising:
an implant adapted to be seated into a first bone or an adjacent second bone;
a distracter contacting at least one of said implant, said first bone or said adjacent second bone;
and a sleeve structured to interpose said implant and said first bone or adjacent second bone, the sleeve releasably covering at least a portion of said implant and adapted to be fully removed from an implant to bone interface without removing said implant from said implant to bone interface as said sleeve pulls said first bone or adjacent second bone to said implant upon advancing and seating of the implant into the first bone or the adjacent second bone, said sleeve having an engagement force on a surface contacting said implant that is different than a surface contacting said first or adjacent second bone, said differential engagement force structured to preferentially move the implant into said first or adjacent second bone, wherein said distracter is structured to displace said sleeve relative to said implant, or displace said implant relative to said sleeve, or displace said implant relative to said first or adjacent second bone.

18. The system of claim 17 further comprising a bone displacer structured to displace the first bone away from the second bone.

19. The system of claim 17 wherein the sleeve comprises a truncated sphere.

20. The sleeve of claim 19 further comprising a plurality of longitudinal serrations having first and second ends, each of said plurality of serrations in spaced apart relationship on said sleeve.

21. The sleeve of claim 20 further comprising a lip extending circumferentially around the truncated sphere at one end thereof.

22. The sleeve of claim 21 wherein said first end of each of said plurality of serrations is proximate said lip.

23. The sleeve of claim 22 wherein said plurality of serrations allow said sleeve to substantially conform to the shape and size of said implant.

24. The sleeve of claim 22 wherein said plurality of serrations allow said lip to break when said implant is seated.

25. The system of claim 19 wherein said sleeve further comprises a plurality of ridges extending circumferentially around said truncated sphere, wherein the surface of said plurality of ridges is grit blast, chemically etched, corrugated or patterned.

26. The sleeve of claim 21 further comprising a plurality of perforations positioned in spaced apart relationship on an end of said truncated sphere opposite said lip.

27. The system of claim 17 further comprising a cup inserter operably connected to said sleeve, said cup inserter including a receiving hole for slidably receiving a broach post mounted to a femoral broach.

28. The system of claim 17 wherein said sleeve comprises at least one material selected from the group consisting of cobalt-chromium alloy, stainless steel, titanium, titanium alloys, Nitinol urethane, polyethylene, expanded polyethylene, nylon, and woven fabric materials.

29. The system of claim 17 further comprising a plurality of sleeves.

30. The system of claim 17 further comprising an alignment guide operably coupled with at least one of said sleeve, said implant, said first bone or said second bone.

31. The system of claim 17 further comprising a surgical tracker operably coupled with at least one of said sleeve, said implant, said first bone or said second bone.

32. The system of claim 1 or 17 wherein the distracter and sleeve are structured to place an implant between adjacent first and second bones and further wherein said distracter is structured to displace said implant towards a final seated position of said implant during which a sleeve to bone engagement force is not exceeded and a relative position of said sleeve to the first and second bone does not significantly change.

33. The system of claim 17 wherein said engagement force is lower on the surface contacting said implant than the surface contacting said first bone or adjacent second bone.

34. A system for seating an implant onto a first bone or adjacent second bone comprising:

an implant adapted to be seated onto a first bone or an adjacent second bone to form an implant to bone interface;

a distracter contacting at least one of said implant, or said first bone or said adjacent second bone;

and a sleeve structured to interpose said implant and said first bone or adjacent second bone and further structured to releasably cover at least a portion of said implant and structured to be releasably removed from the implant to bone interface as said sleeve pulls said first bone or adjacent second bone to said implant upon advancing and seating of the implant onto the first bone or adjacent second bone, said sleeve having an engagement force on a surface contacting said implant that is different than a surface contacting said first or second bone, said differential engagement force structured to preferentially move the implant onto said first bone or adjacent second bone, wherein said distracter is structured to displace said sleeve relative to said first or second bone, or displace said implant relative to said sleeve, or displace said implant relative to the first or adjacent second bone.

35. The system of claim 34 further comprising a bone displacer structured to displace the first bone away from the second bone.

36. The system of claim 34 wherein the sleeve comprises a truncated sphere.

37. The sleeve of claim 36 further comprising a plurality of longitudinal serrations having first and second ends, each of said plurality of serrations in spaced apart relationship on said sleeve.

38. The sleeve of claim 37 further comprising a lip extending circumferentially around the truncated sphere at one end thereof.

39. The sleeve of claim 38 wherein said first end of each of said plurality of serrations is proximate said lip.

40. The sleeve of claim 39 wherein said plurality of serrations allow said sleeve to substantially conform to the shape and size of said implant.

41. The sleeve of claim 39 wherein said plurality of serrations allow said lip to break when said implant is seated.

42. The sleeve of claim 36 wherein said sleeve further comprises a plurality of ridges extending circumferentially around said truncated sphere, wherein the surface of said plurality of ridges is grit blast, chemically etched, corrugated or patterned.

43. The sleeve of claim 38 further comprising a plurality of perforations positioned in spaced apart relationship on an end of said truncated sphere opposite said lip.

44. The system of claim 34 further comprising a cup inserter operably connected to said sleeve, said cup inserter including a receiving hole for slidably receiving a broach post mounted to a femoral broach.

45. The system of claim 34 wherein said sleeve comprises at least one material selected from the group consisting of cobalt-chromium alloy, stainless steel, titanium, titanium alloys, Nitinol urethane, polyethylene, expanded polyethylene, nylon, and woven fabric materials.

46. The system of claim 34 further comprising a plurality of sleeves.

47. The system of claim 34 further comprising an alignment guide operably coupled to said sleeve.

48. The system of claim 34 further comprising a surgical tracker operably coupled to said sleeve.

49. The system of claims 1, 17 or 34 wherein said sleeve is of unitary construction.

50. The system of claims 1, 17 or 34 wherein said sleeve has a first surface structured to engage said implant.

51. The system of claims 1, 17, or 34 wherein said sleeve has a second surface structured to engage said first or second bone.

52. The system of claims 1, 17 or 34 further comprising an alignment guide structured to operably coupled to said implant.

53. The system of claim 14 wherein said alignment guide include alignment rods for providing a geometric reference between said implant and said first and second bones to align and orient the implant.

54. The system of claim 34 wherein said engagement force is higher on the surface contacting said implant than the surface contacting said first or adjacent second bone.

55. A system for seating an implant into a bone cavity or onto a bone comprising: an implant structured to be seated into a bone cavity having first and second bones or onto a first bone or adjacent second bone to form an implant to bone interface; a distracter; and a sleeve structured to releasably cover at least a portion of said implant and structured to be removed from the implant to bone interface as said sleeve pulls said first bone or adjacent second bone to said implant upon advancing and seating of the implant into the bone cavity or onto the bone, the sleeve having a first surface in communication with said implant and a second surface in communication with said first or adjacent second bone wherein said distracter is in communication with said implant, said first bone, adjacent second bone or said sleeve and further wherein the engagement force is higher between the sleeve and the bone than between the sleeve and the implant when the implant is seated into a bone cavity and further wherein the engagement force is lower between the sleeve and the bone than between the sleeve and the implant when the implant is seated onto a bone.

56. The system of claim 55 further comprising a bone displacer in communication with said distracter; said bone displacer structured to displace the bone away from an adjacent second bone.

57. The system of claim 55 further comprising an alignment guide in communication with said sleeve, said implant or said bone.

58. The system of claim 55 further comprising a surgical tracker in communication with said sleeve, said implant or said bone.

* * * * *